(12) United States Patent
Matsui et al.

(10) Patent No.: US 10,568,523 B2
(45) Date of Patent: Feb. 25, 2020

(54) HEAT MONITORING INSTRUMENT AND THERMAL THERAPY APPARATUS

(71) Applicant: OLYMPUS CORPORATION, Tokyo (JP)

(72) Inventors: Shoichi Matsui, Sagamihara (JP); Kenichi Nishina, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1036 days.

(21) Appl. No.: 14/952,050

(22) Filed: Nov. 25, 2015

(65) Prior Publication Data

US 2016/0073896 A1 Mar. 17, 2016

Related U.S. Application Data

(63) Continuation of application No. PCT/JP2014/084300, filed on Dec. 25, 2014.

(30) Foreign Application Priority Data

Mar. 13, 2014 (JP) .................. 2014-050571

(51) Int. Cl.
*A61B 5/01* (2006.01)
*A61F 7/12* (2006.01)
(Continued)

(52) U.S. Cl.
CPC .................. *A61B 5/01* (2013.01); *A61F 7/12* (2013.01); *A61B 18/04* (2013.01);
(Continued)

(58) Field of Classification Search
CPC ............ A61B 5/01; A61B 2017/00084; A61B 2018/00642; A61B 2018/00791;
(Continued)

(56) References Cited

U.S. PATENT DOCUMENTS 5,885,258 A 3/1999 Sachdeva et al.
5,964,791 A 10/1999 Bolmsjo
(Continued)

FOREIGN PATENT DOCUMENTS

JP 2-124438 A 5/1990
JP 8-308853 A 11/1996
(Continued)

OTHER PUBLICATIONS

Extended Supplementary European Search Report dated Feb. 17, 2017 in related European Patent Application No. 14 88 5802.0.
(Continued)

*Primary Examiner* — Kaitlyn E Smith
(74) *Attorney, Agent, or Firm* — Scully, Scott, Murphy & Presser, P.C.

(57) ABSTRACT

A heat monitoring instrument of the invention includes: an insertion portion for inserting into tissue of a subject; a distal end portion that constitutes a distal end portion of the insertion portion and receives and transmits heat of the subject into which the insertion portion is inserted; and a shape-memory portion that constitutes the distal end portion and changes shape due to the heat of the subject.

6 Claims, 24 Drawing Sheets

(51) Int. Cl.
*A61B 18/04* (2006.01)
*A61N 7/02* (2006.01)
*A61B 17/00* (2006.01)
*A61N 7/00* (2006.01)
*A61B 18/00* (2006.01)
*A61F 7/00* (2006.01)

(52) U.S. Cl.
CPC ............... *A61B 2017/00084* (2013.01); *A61B 2018/00642* (2013.01); *A61B 2018/00791* (2013.01); *A61F 2007/0095* (2013.01); *A61N 7/02* (2013.01); *A61N 2007/0047* (2013.01); *A61N 2007/025* (2013.01)

(58) Field of Classification Search
CPC ..... A61F 7/12; A61N 7/02; A61N 2007/0047; A61N 2007/025
See application file for complete search history.

(56) References Cited

U.S. PATENT DOCUMENTS

| | | | | |
|---|---|---|---|---|
| 7,182,761 B2* | 2/2007 | Garabedian | ........ | A61B 18/1477 606/41 |
| 7,347,863 B2* | 3/2008 | Rothe | ................. | A61B 1/0014 606/139 |
| 2002/0128650 A1* | 9/2002 | McClurken | ........ | A61B 18/1442 606/48 |
| 2003/0014094 A1 | 1/2003 | Hammack et al. | | |
| 2003/0114843 A1 | 6/2003 | Lafontaine | | |
| 2011/0184310 A1* | 7/2011 | Brown | ................. | A61B 17/221 600/549 |
| 2011/0276047 A1* | 11/2011 | Sklar | ................. | A61B 18/1492 606/41 |
| 2013/0158414 A1 | 6/2013 | Sachdeva et al. | | |
| 2013/0261368 A1 | 10/2013 | Schwartz | | |
| 2016/0045245 A1* | 2/2016 | Matsui | ................... | A61B 18/02 606/20 |

FOREIGN PATENT DOCUMENTS

| | | |
|---|---|---|
| JP | 11-505155 A | 5/1999 |
| JP | 2005-512633 A | 5/2005 |
| WO | WO 96/36288 A1 | 11/1996 |
| WO | WO 03/051214 A1 | 6/2003 |

OTHER PUBLICATIONS

International Search Report dated Mar. 31, 2015 issued in PCT/JP2014/084300.

* cited by examiner

HEAT MONITORING INSTRUMENT AND THERMAL THERAPY APPARATUS

CROSS REFERENCE TO RELATED APPLICATION

This application is a continuation application of PCT/JP2014/084300 filed on Dec. 25, 2014 and claims benefit of Japanese Application No. 2014-050571 filed in Japan on Mar. 13, 2014, the entire contents of which are incorporated herein by this reference.

BACKGROUND OF THE INVENTION

1. Field of the Invention

The present invention relates to a heat monitoring instrument that monitors the state of an increase in the temperature of tissue of a subject when executing thermal therapy, and a thermal therapy apparatus.

2. Description of the Related Art

Thermal therapy is known that is performed with respect to tissue of an organism such as a human where the subject's tissue is heated. Thermal therapy, for example, causes tissue to generate heat by applying a high-frequency voltage, microwaves radio waves or by irradiation of ultrasound with respect to tissue from a thermal therapy instrument inserted into the body of the subject. As disclosed in, for example, Japanese Patent Application Laid-Open Publication No. 8-308853, thermal therapy is used for therapy that kills tumor cells in tissue and the like.

In the case of heating tissue by thermal therapy, heat is conveyed to the therapy object and to tissue surrounding the therapy object, where it is desirable to avoid a situation in which the heating affects tissue that is not the therapy object. Consequently, a technique is proposed that monitors the temperature of tissue using thermography or a thermocouple when executing thermal therapy.

SUMMARY OF THE INVENTION

A heat monitoring instrument according to one aspect of the present invention includes: an insertion portion for inserting into tissue of a subject; a distal end portion that constitutes a distal end portion of the insertion portion, the distal end portion receiving and transmitting heat of the subject into which the insertion portion is inserted; and a shape-memory portion that constitutes the distal end portion and changes shape due to the heat of the subject.

A thermal therapy apparatus according to one aspect of the present invention includes: the heat monitoring instrument, a thermal therapy instrument that heats the tissue, and a drive apparatus that actuates the thermal therapy instrument; wherein the drive apparatus stops operation of the thermal therapy instrument in a case where a change in shape of the heat monitoring instrument is detected.

DETAILED DESCRIPTION OF THE PREFERRED EMBODIMENTS

Figure 1:
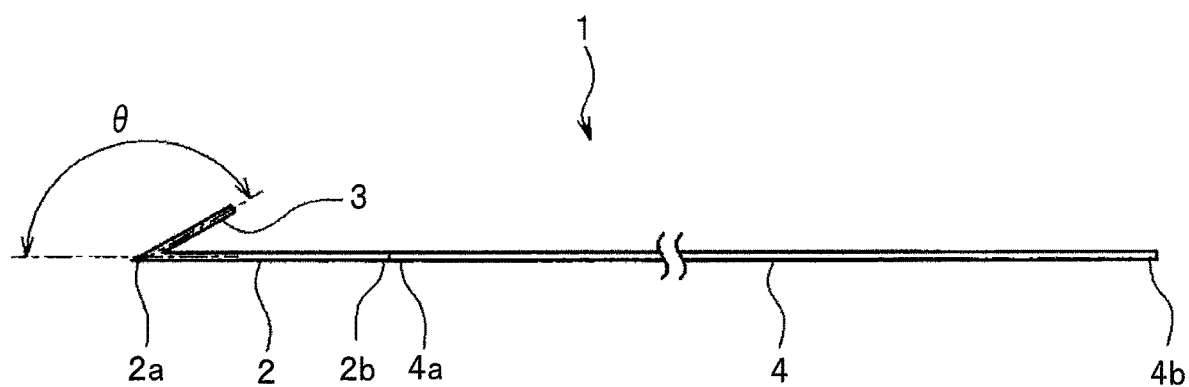
FIG. 1 is a view illustrating a configuration of a heat monitoring instrument according to a first embodiment.

Preferred embodiments of the present invention are described hereunder with reference to the accompanying drawings. Note that the respective components in the respective drawings used for the following description are displayed in a contraction scale which differs according to each component so as to be shown in a size that is recognizable in the drawings, and the present invention is not limited only to the quantity of components, the shapes of components, the ratios between the sizes of components, and the relative positional relationships between the respective components illustrated in the drawings.

First Embodiment

A heat monitoring instrument 1 of the present embodiment that is shown in FIG. 1 is an apparatus that, when performing thermal therapy that heats predetermined tissue with respect to an organism such as a human as a subject, allows a user to perceive the state of a change in temperature in peripheral tissue accompanying the thermal therapy.

The heat monitoring instrument 1 includes an insertion portion 2, a locking portion 3 that is provided in the insertion portion 2, and a linear member 4 that is coupled to the insertion portion 2.

The linear member 4 is an elongated member having a linear shape that is made of metal, resin, fiber or the like. The shape and material of the linear member 4 is not particularly limited as long as the linear member 4 is a member that withstands a tensile force (a tensile force that is applied in a longitudinal direction) of a predetermined size. For example, the linear member 4 may be of a form that, like string, easily buckles and changes shape in a case where a compressive force is applied in the longitudinal direction. Further, for example, the linear member 4 may be of a form that, like a piece of wire, even in a case where a compressive force is applied in the longitudinal direction, does not buckle until the compressive force exceeds a predetermined value. That is, as long as the linear member 4 is a member that transmits a tensile force in a longitudinal direction, the linear member 4 may be of a form that transmits a compressive force, or may be of a form that does not transmit a compressive force in the longitudinal direction.

Note that, although the thickness in the longitudinal direction of the linear member 4 of the present embodiment that is shown in the drawings is fixed, the linear member 4 may also have a shape in which the cross-sectional shape in the longitudinal direction changes. Further, the linear member 4 need not be constituted by only a single member, and may be constituted by a plurality of members. For example, the linear member 4 may have a form in which a plurality of members are present within the same cross-section, like twine, or may have a form in which a plurality of members are connected in the longitudinal direction, like a chain.

A distal end portion 4a that is one end part of the linear member 4 is coupled to the insertion portion 2. Note that, the linear member 4 and the insertion portion 2 may also be formed integrally by a single member.

The insertion portion 2 is a part that is inserted into tissue of an organism such as a human as the subject, or into a conduit that is provided in an endoscope or a cylindrical member that can be introduced into the body of an organism, such as a needle tube that can be pierced into the tissue of an organism.

The locking portion 3 is provided in the insertion portion 2. As described later, the external shape of the insertion portion 2 differs between a case where the temperature thereof is less than or equal to a predetermined temperature and a case where the temperature thereof is in a predetermined temperature range that exceeds the predetermined temperature. Note that, it is sufficient that the insertion portion 2 has a structure that changes shape in a case where the insertion portion 2 is heated from a state of the predetermined temperature or less to a temperature in the predetermined temperature range, and the insertion portion 2 need not change shape in a case where the temperature thereof falls from the state in the predetermined temperature range to the predetermined temperature or less. That is, a change in shape caused by a change in the temperature of the insertion portion 2 may be irreversible.

In a case where the insertion portion 2 is inserted into the tissue of an organism and the temperature of the insertion portion 2 is less than or equal to the predetermined temperature, the locking portion 3 engages with the surrounding tissue. In this case, if a force in a direction to withdraw the insertion portion 2 from inside the tissue is applied to the insertion portion 2, the locking portion 3 generates a resistance force that retains the insertion portion 2 inside the tissue against the aforementioned force. Further, in a case where the insertion portion 2 is inserted to a predetermined position inside the cylindrical member and the temperature of the locking portion 3 is less than or equal to the predetermined temperature, the locking portion 3 engages with an engagement portion that is provided in the cylindrical member. If a force in a direction to withdraw the insertion portion 2 from inside the tissue is applied to the insertion portion 2, the locking portion 3 generates a resistance force that retains the insertion portion 2 inside the cylindrical member against the aforementioned force.

That is, in a case where the insertion portion 2 is inserted inside tissue or into the cylindrical member and the temperature of the insertion portion 2 is less than or equal to a predetermined temperature, even if a tensile force is applied to the linear member 4 by pulling the proximal end side of the linear member 4, because the locking portion 3 is engaged with the tissue or the cylindrical member, the insertion portion 2 stays inside the tissue or inside the cylindrical member. Note that, if an excessive tensile force of an extent such that the locking portion 3, the tissue or the cylindrical member deforms greatly or breaks is applied to the linear member 4, naturally the insertion portion 2 will drop out.

Further, in a case where the insertion portion 2 is inserted into tissue of an organism and the insertion portion 2 is heated from a state of the predetermined temperature or less to the predetermined temperature range, the insertion portion 2 changes shape and the locking function of the locking portion 3 disappears, and the engagement between the locking portion 3 and the tissue or the cylindrical member is released.

That is, in a case where the insertion portion 2 is inserted into tissue or into the cylindrical member, and the insertion portion 2 is heated to the predetermined temperature range, if a tensile force is applied to the linear member 4 by pulling the proximal end side of the linear member 4, the insertion portion 2 will come out from inside the tissue or inside the cylindrical member.

Next, a specific configuration of the insertion portion 2 and the locking portion 3 will be described. As one example according to the present embodiment, the insertion portion 2 has a form that is to be inserted into tissue of an organism such as a human that is the subject. FIG. 1 illustrates a case where the temperature of the locking portion 3 is less than or equal to a predetermined temperature.

As shown in FIG. 1, the insertion portion 2 of the present embodiment is composed of a member having a linear shape. The locking portion 3 is provided at a distal end portion 2a that is one end portion of the insertion portion 2. A proximal end portion 2b that is the other end portion of the insertion portion 2 is coupled to the distal end portion 4a of the linear member 4. The insertion portion 2 according to the present embodiment is made of a shape-memory alloy that changes shape when heated to a predetermined temperature range that exceeds a predetermined temperature.

When the temperature of the insertion portion 2 is less than or equal to the predetermined temperature, the locking portion 3 has a shape such that the distal end portion 2a of the insertion portion 2 that is made of a shape-memory alloy that has a linear shape bends backwards.

Specifically, as indicated by reference symbol θ in FIG. 1, the locking portion 3 has a shape in which the insertion portion 2 bends at an angle of 90 or more at a position that is a predetermined length from the distal end of the insertion portion 2. That is, the locking portion 3 has a hook-like shape in a case where the temperature of the insertion portion 2 is less than or equal to a predetermined temperature. This kind of shape of the locking portion 3 is referred to as a "barb" or the like with respect to a fish hook or an arrowhead.

Hence, in a case where the insertion portion 2 is inserted inside the tissue of an organism such as a human as a subject, and the temperature of the insertion portion 2 is less than or equal to a predetermined temperature, the locking portion 3 that has a hook shape engages with the surrounding tissue.

Note that, although in the present embodiment that is illustrated in the drawings a bent portion of the locking portion 3 is substantially a V-shape, the bent portion may be substantially a U-shape that is rounded.

Figure 2:
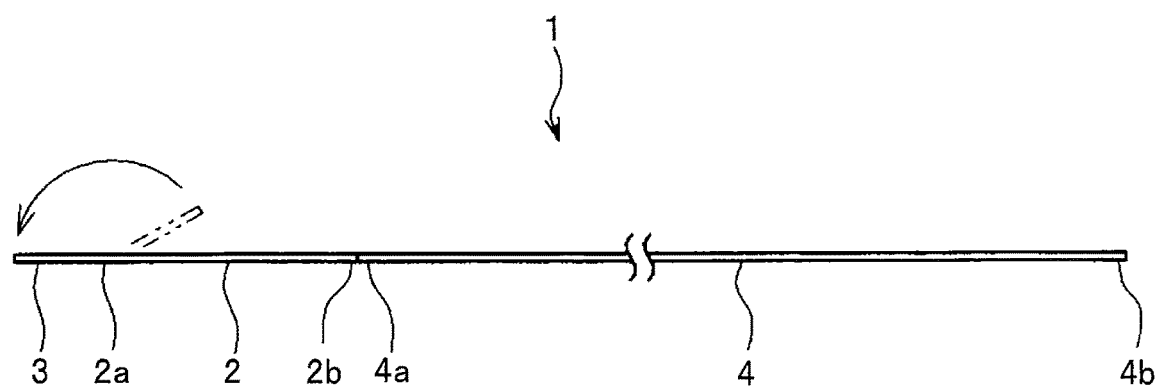
FIG. 2 is a view illustrating a state in which a locking portion changes shape in the heat monitoring instrument of the first embodiment.

In a case where the insertion portion 2 is heated from a state in which the insertion portion 2 is a predetermined temperature to a predetermined temperature range that exceeds the predetermined temperature, as shown in FIG. 2, the insertion portion 2 changes shape so as to eliminate the bend in the insertion portion 2. That is, in a state in which the insertion portion 2 is heated to the predetermined temperature range and changes shape, the locking portion 3 runs along the longitudinal direction of the insertion portion 2, and the locking portion 3 and the insertion portion 2 become a rectilinear shape.

Hence, in a case where the insertion portion 2 is inserted into the tissue of an organism such as a human as the subject, and the insertion portion 2 is heated from a state in which the insertion portion 2 is the predetermined temperature or less to a temperature in the predetermined temperature range, the locking portion 3 that is a hook shape changes shape into a rectilinear shape to thereby release the engagement with the tissue.

A value of the predetermined temperature in this case is not particularly limited, and is arbitrarily set according to the conditions under which the heat monitoring instrument 1 is used. As one example in the present embodiment, the predetermined temperature is set from 42° C. to 45° C. A predetermined temperature from 42° C. to 45° C. is a temperature at which tumor cells are killed, but at which healthy cells survive. Note that the predetermined temperature may also be less than 42° C. or may exceed 45° C.

Figure 3:
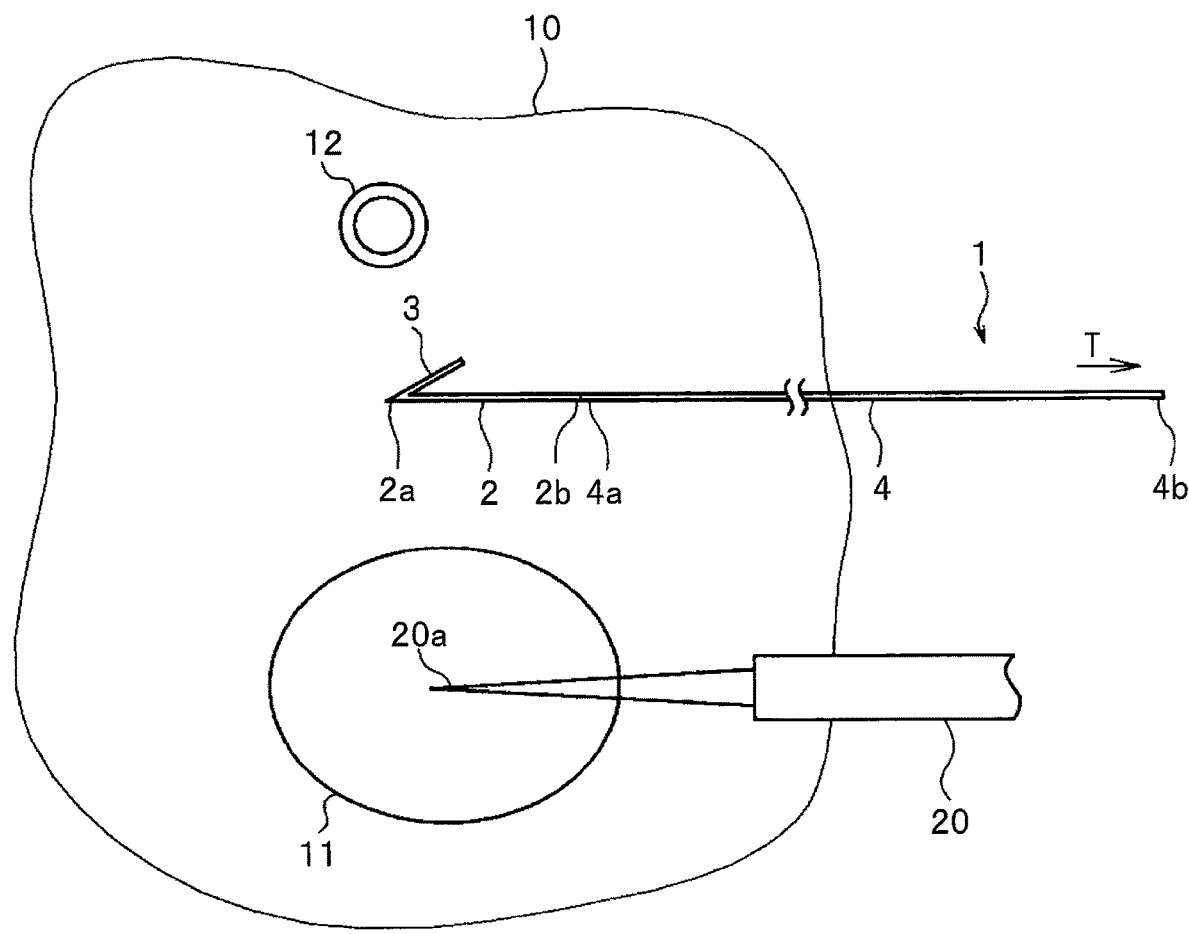
FIG. 3 is a schematic diagram illustrating a state in which the heat monitoring instrument of the first embodiment is inserted into tissue.

Next, the action of the heat monitoring instrument 1 of the present embodiment will be described. FIG. 3 is a schematic diagram illustrating the manner in which thermal therapy is performed on tissue of an organism that includes tumor cells. FIG. 3 illustrates a cross-section of certain tissue 10 of an organism such as a human, and a target site 11 that is composed of tumor cells or the like as a therapy object exists at the cross-section in question. Note that, the object of thermal therapy may be a malignant tumor such as pancreatic cancer, hepatic cancer, renal cancer, lung cancer, prostatic cancer or malignant lymphoma, or may be a benign tumor such as uterine myoma or endometriosis.

In the thermal therapy, the target site 11 is heated by a thermal therapy instrument 20 that is inserted into the tissue 10 or by the thermal therapy instrument 20 that is disposed outside of the tissue 10. In this case, the thermal therapy instrument 20 is an apparatus that causes the tissue 10 to generate heat by application of a high-frequency voltage such as microwaves or radio waves or by irradiation of ultrasound. As one example according to the present embodiment, it is assumed that tissue that is present around a distal end portion 20a of the thermal therapy instrument 20 is heated by an operation of the thermal therapy instrument 20 that is inserted inside the target site 11. Note that, so-called "high-intensity focused ultrasound (HIFU)" in which ultrasound is irradiated from the thermal therapy instrument 20 so as to focus on the target site 11 is known as a method for causing the target site 11 to generate heat by means of the thermal therapy instrument 20 that is disposed outside the tissue 10. The specific configuration of the thermal therapy instrument 20 is known, and a detailed description thereof is therefore omitted herein.

Before performing thermal therapy, the insertion portion 2 of the heat monitoring instrument 1 is inserted into the tissue 10, and the locking portion 3 is disposed at a location at which it is desired to detect the state of a change in temperature inside the tissue 10. As one example according to the present embodiment, the location at which the locking portion 3 is disposed so as to detect the state of a change in temperature inside the tissue 10 is between the distal end portion 20a of the thermal therapy instrument 20 and a blood vessel 12. Note that the location at which the locking portion 3 is disposed is not limited thereto, and may be a boundary portion between the target site 11 that is the tumor cells and the healthy cells, or may be inside the target site 11.

The insertion path of the insertion portion 2 into the tissue 10 may be a path that passes through the skin from outside the body of the subject, or a path that passes from inside the digestive tract of the subject through a tubular wall of the digestive tract, or may be a path that passes from inside a body cavity through an outer wall of an internal organ having the tissue 10. An operation to insert the insertion portion 2 of the heat monitoring instrument 1 to a predetermined position inside the tissue 10 is performed, for example, under observation by means of an ultrasound diagnostic apparatus such as an ultrasound endoscope.

In a state in which the insertion portion 2 of the heat monitoring instrument 1 is inserted inside the tissue 10, a proximal end portion 4b of the linear member 4 is extended to outside of the internal organ that has the tissue 10. The proximal end portion 4b of the linear member 4 may also be extended as far as outside the body of the subject in a state in which the insertion portion 2 is inserted inside the tissue 10.

In a state in which the insertion portion 2 of the heat monitoring instrument 1 is inserted inside the tissue 10 and the locking portion 3 is disposed inside the tissue 10 (state shown in FIG. 3), because the temperature of the insertion portion 2 is lower than the predetermined temperature that is 42° C. to 45° C., the locking portion 3 engages with the surrounding tissue 10. Consequently, even in a case where a tensile force T is applied to the proximal end portion 4b side of the linear member 4, and a force is applied to the insertion portion 2 in a direction to withdraw the insertion portion 2 from inside the tissue 10, the position of the insertion portion 2 inside the tissue 10 does not change.

That is, in a case where the temperature of the tissue 10 in which the locking portion 3 is disposed is less than or equal to the predetermined temperature, even if the linear member 4 that extends to outside the tissue 10 is pulled by a finger of the user or by an apparatus of some kind, the heat monitoring instrument 1 will remain inserted inside the tissue 10. In other words, in a case where the insertion portion 2 of the heat monitoring instrument 1 does not drop out from inside the tissue 10 even when the tensile force T is applied to the linear member 4, the user can determine that the temperature of the tissue 10 at the location at which the insertion portion 2 is disposed is less than or equal to the predetermined temperature.

Figure 4:
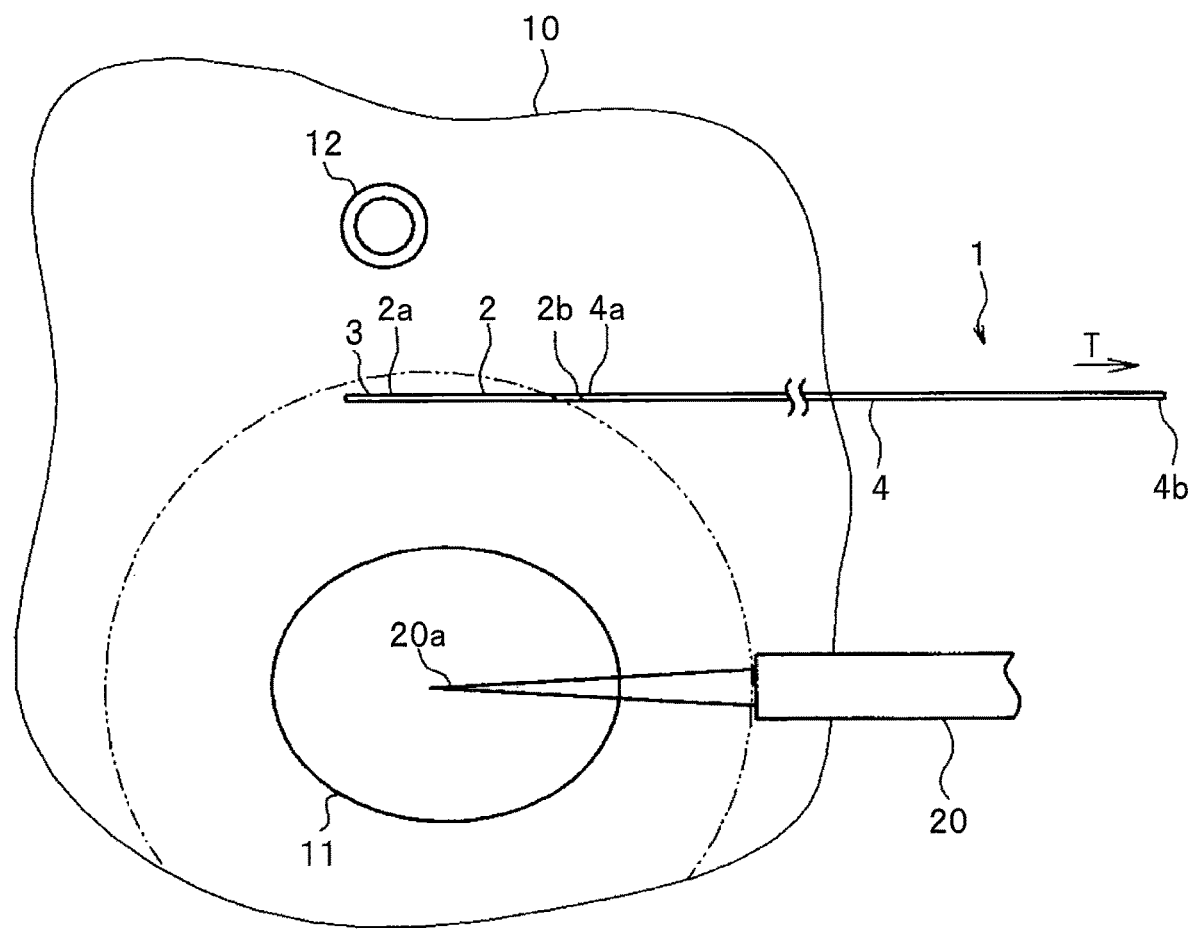
FIG. 4 is a view illustrating the manner of performing thermal therapy using the heat monitoring instrument of the first embodiment.

When the thermal therapy instrument 20 is actuated to start thermal therapy, the tissue 10 around the distal end portion 20a of the thermal therapy instrument 20 generates heat. Because heat that is generated by operation of the thermal therapy instrument 20 is transmitted to the surrounding tissue 10, a region in which the temperature of the tissue 10 exceeds the predetermined temperature (42° C. to 45° C.) spreads to the surrounding area as time passes from the start of thermal therapy. In FIG. 4, a region in which the temperature of the tissue 10 exceeds the predetermined temperature is indicated by a dashed line.

Further, as shown in FIG. 4, when the region in which the temperature of the tissue 10 exceeds the predetermined temperature extends as far as the location at which the insertion portion 2 is disposed, the locking portion 3 changes shape and the engagement between the locking portion 3 and the tissue 10 is released. Consequently, in a case where a tensile force T is applied to the proximal end portion 4b side of the linear member 4 and a force is applied to the insertion portion 2 in a direction to withdraw the insertion portion 2 from inside the tissue 10, the insertion portion 2 drops out from the tissue 10.

That is, in a case where the temperature of the tissue 10 at which the insertion portion 2 is disposed is heated up to the predetermined temperature range that exceeds the predetermined temperature, if the linear member 4 that extends to outside of the tissue 10 is pulled by a finger of the user or by some kind of apparatus, the heat monitoring instrument 1 will be withdrawn from the tissue 10. In other words, in a case where the tensile force T is applied to the linear member 4 and as a result the insertion portion 2 of the heat monitoring instrument 1 drops out from inside the tissue 10, the user can determine that the tissue 10 at the location at which the insertion portion 2 is disposed has been heated up to the predetermined temperature range.

An example of performing thermal therapy with respect to a pancreas 13 that has the tissue 10 in which the target site 11 that is composed of tumor cells is present will now be described referring to FIG. 5. In the example illustrated in FIG. 5, in a state in which the human that is the subject reclines on the left side, an ultrasound endoscope 30 is inserted into the stomach 14 that is part of the digestive tract, and thermal therapy is performed on the pancreas 13 from inside the stomach 14 using the thermal therapy instrument 20 that is protruded from a distal end portion 31a of the ultrasound endoscope 30.

The configuration of the ultrasound endoscope 30 as well as the thermal therapy that is performed using the ultrasound endoscope 30 and the thermal therapy instrument 20 are known, and hence a detailed description is omitted here.

The ultrasound endoscope 30 has an insertion portion 31 that can be introduced into inside the subject, and an operation portion 32 that is located at a proximal end of the insertion portion 31. An ultrasound transducer 31b for sending and receiving ultrasound, an image pickup apparatus for picking up optical images, an illumination apparatus, and a distal-end-side opening portion 31c of a treatment instrument channel 34 and the like are provided at the distal end portion 31a of the insertion portion 31.

An ultrasound image obtained by driving the ultrasound transducer 31b and an optical image obtained by driving the image pickup apparatus are displayed on an unshown image display apparatus that is connected through a universal cord 33 that extends from the operation portion 32.

The treatment instrument channel 34 is a conduit that is inserted through the inside of the insertion portion 31. A proximal-end-side opening portion 34b of the treatment instrument channel 34 opens at the operation portion 32. By inserting the thermal therapy instrument 20 into the treatment instrument channel 34 from the proximal-end-side opening portion 34b, the distal end portion 20a of the thermal therapy instrument 20 can be protruded from the distal-end-side opening portion 34a.

Figure 5:
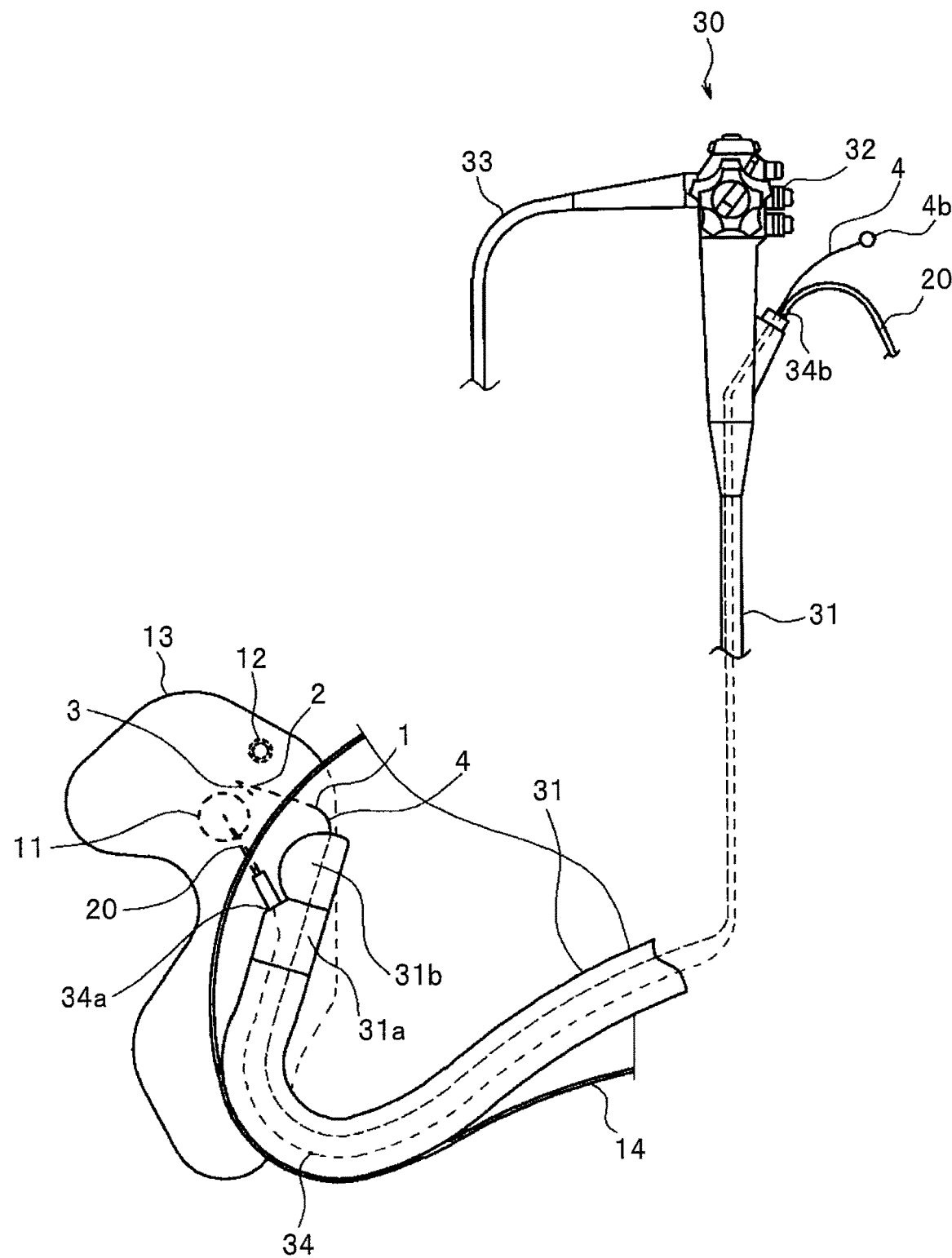
FIG. 5 is a view illustrating an example of thermal therapy.

According to the thermal therapy shown in FIG. 5, the insertion portion 31 of the ultrasound endoscope 30 is inserted into the stomach 14, and under observation by means of an optical image and an ultrasound image using the ultrasound endoscope 30, the insertion portion 2 of the heat monitoring instrument 1 is inserted from inside the stomach 14 into the tissue 10 of the pancreas 13. As described above, according to the present embodiment the insertion portion 2 is disposed between the target site 11 and the blood vessel 12. In this case, the liner member 4 extends to outside the body of the subject via a conduit provided in the ultrasound endoscope 30.

The conduit through which the linear member 4 is inserted until the linear member 4 exits to outside the body of the subject may be the treatment instrument channel 34 through which the thermal therapy instrument 20 is inserted, or may be a conduit that is provided in the ultrasound endoscope 30 separately from the treatment instrument channel 34. Further, the conduit through which the linear member 4 is inserted may be a cylindrical member that is inserted inside the subject separately from the ultrasound endoscope 30.

A tensile force T can be applied to the linear member 4 that is extended to outside the body of the subject, by, for example, the user using a finger to grasp the proximal end portion 4b. Further, for example, a tensile force T can be applied to the linear member 4 by a method that fixes a weight having a predetermined weight to the proximal end portion 4b, or by a method that connects a pulling apparatus that uses a spring, an electric motor or the like to the proximal end portion 4b.

Further, the thermal therapy instrument 20 is protruded from the distal-end-side opening portion 34a that is provided in the distal end portion 31a of the insertion portion 31. The thermal therapy instrument 20 is inserted into the tissue 10 of the pancreas 13 from inside the stomach 14, and thermal therapy that heats the tumor cells 11 is started.

Subsequently, upon the temperature of the insertion portion 2 being heated up to the predetermined temperature range that exceeds the predetermined temperature as a result of heat of the thermal therapy being transmitted to the surrounding area, the insertion portion 2 changes shape and the engagement between the locking portion 3 and the tissue 10 is released, and consequently the insertion portion 2 drops out from the tissue 10. Withdrawal of the insertion portion 2 from the tissue 10 can be confirmed, for example, by observation by means of an optical image and an ultrasound image using the ultrasound endoscope 30. In a case where the linear member 4 is pulled by a finger of the user, the user can directly perceive withdrawal of the insertion portion 2 from the tissue 10 as a result of the tensile force that was being applied to the linear member 4 fading. By confirming the withdrawal of the insertion portion 2 from the tissue 10, the user can determine that the tissue 10 at the location at which the insertion portion 2 had been disposed is heated to the predetermined temperature range.

Figure 6:
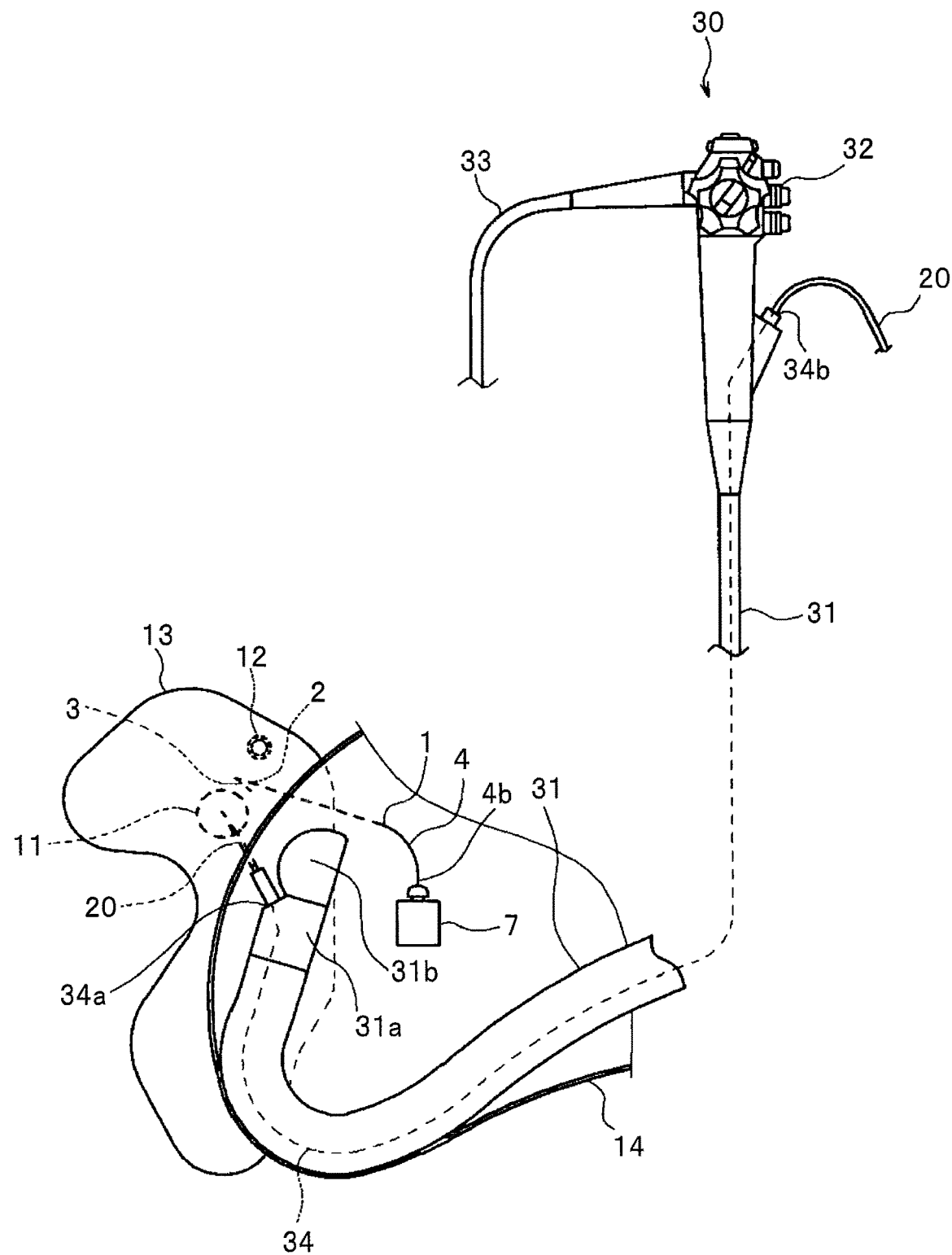
FIG. 6 is a view illustrating another example of thermal therapy.

In this connection, although according to the example illustrated in FIG. 5 the proximal end portion 4b of the linear member 4 extends to outside the body of the subject in a state in which the insertion portion 2 of the heat monitoring instrument 1 is inserted inside the tissue 10 of the pancreas 13, as illustrated as one example in FIG. 6, a form may also be adopted in which the proximal end portion 4b of the linear member 4 extends to inside the body of the subject (into the stomach 14).

In the example illustrated in FIG. 6, the insertion portion 31 of the ultrasound endoscope 30 is inserted into the stomach 14, and under observation by means of an optical image and an ultrasound image using the ultrasound endoscope 30, the insertion portion 2 of the heat monitoring instrument 1 is inserted into the tissue 10 of the pancreas 13 from inside the stomach 14. As described above, in the present embodiment the insertion portion 2 is disposed between the tumor cells 11 and the blood vessel 12. In this case, the proximal end portion 4b of the linear member 4 extends as far as the inside of the stomach 14.

A weight 7 is fixed to the linear member 4 that extends as far as the inside of the stomach 14. A tensile force T is applied to the linear member 4 as a result of the weight 7 being fixed to the linear member 4. That is, the weight 7 is a pulling apparatus that produces a force in a direction to withdraw the insertion portion 2 of the heat monitoring instrument 1 from the tissue 10. Note that, the weight 7 may also be integrated with the proximal end portion 4b of the linear member 4.

The thermal therapy instrument 20 is then protruded from the distal-end-side opening portion 34a that is provided in the distal end portion 31a of the insertion portion 31, the thermal therapy instrument 20 is inserted into the tissue 10 of the pancreas 13 from inside the stomach 14, and the thermal therapy for heating the target site 11 is started.

Subsequently, upon the temperature of the locking portion 3 being heated to the predetermined temperature range that exceeds the predetermined temperature as a result of the heat of the thermal therapy being transmitted to the surrounding area, the locking portion 3 changes shape and the engagement between the locking portion 3 and the tissue 10 is released, and consequently the insertion portion 2 drops out from the tissue 10. Withdrawal of the insertion portion 2 from the tissue 10 can be confirmed, for example, by observation by means of an optical image and an ultrasound image using the ultrasound endoscope 30. By confirming withdrawal of the insertion portion 2 from the tissue 10, the user can determine that the tissue 10 at the location at which the insertion portion 2 is disposed is heated up to the predetermined temperature range.

As described above, according to the present embodiment, when performing thermal therapy, by using the heat monitoring instrument 1 the user can easily and reliably know the state of an increase in the temperature of tissue at a desired location during performance of the thermal therapy. Further, because the heat monitoring instrument 1 of the present embodiment has a simple structure in which the locking portion 3 is provided in the insertion portion 2 that is made of a shape-memory alloy, and the linear member 4 is coupled to the insertion portion 2, the heat monitoring instrument 1 can be manufactured at a low cost.

For example, in a case where the locking portion 3 is disposed between the target site 11 and the blood vessel 12 as in the present embodiment and thermal therapy is performed while applying the tensile force T to the linear member 4, if the thermal therapy is stopped when the insertion portion 2 comes out from the tissue 10, it is possible to prevent the blood vessel 12 from being heated to a temperature that exceeds the predetermined temperature. As described above, because the predetermined temperature is a temperature at which tumor cells are killed and healthy cells survive, the heating by the thermal therapy does not affect the blood vessel 12. Thus, by using the heat monitoring instrument 1 in thermal therapy that kills tumor cells, heating by the thermal therapy can be prevented from affecting normal tissue around the target site 11 that is composed of the tumor cells.

Note that, in addition to the above described use, the heat monitoring instrument 1 of the present embodiment can also be used to allow a user to perceive whether or not tissue is heated to a temperature that exceeds the predetermined temperature by thermal therapy in order to determine whether or not thermal therapy has been sufficiently performed. Hence, when using the heat monitoring instrument 1, a location at which the locking portion 3 is disposed inside the tissue 10 is not limited to the above described embodiment, and may be appropriately decided according to the use.

For example, if the locking portion 3 is disposed in the vicinity of the outside of the target site 11, if the insertion portion 2 drops out the user can determine that the entire target site 11 is heated to a temperature at which tumor cells are killed.

Further, for example, if the tissue 10 in which the target site 11 is present is a site that is sensitive to heating, such as the pancreas, in some cases it is desired to prevent healthy tissue on the outside of the target site 11 from being heated so as to suppress side effects that are caused by thermal therapy. In this case, if the locking portion 3 is disposed at a position in the vicinity of the outer circumference of the target site 11 that is a position that is inside the target site 11, an increase in the temperature of the tissue 10 outside the target site 11 can be prevented.

The heat monitoring instrument 1 that is described above is an apparatus that perceives a temperature change in tissue of a subject by means of a change in shape of the insertion portion 2 that is made of a shape-memory alloy. Although in the present embodiment the heat monitoring instrument 1 is used in a case of heating the tissue of a subject, the heat monitoring instrument 1 can also be used for cryotherapy that freezes the tissue of a subject. In this case, the insertion portion 2 of the heat monitoring instrument 1 is configured so as to change shape so that engagement between the locking portion 3 and the tissue is released if the temperature falls below a predetermined temperature, for example, 0° C.

Next, a modification of the insertion portion 2 and the locking portion 3 will be described. Although the above-described locking portion 3 is a hook-like shape, the locking portion 3 is not limited thereto. The locking portion 3 may be a portion having a shape that, in a case where the insertion portion 2 is inserted into the tissue 10 of an organism and the temperature of the insertion portion 2 is less than or equal to the predetermined temperature, produces a force that retains the insertion portion 2 inside the tissue 10 against a force in a direction to withdraw the insertion portion 2, and changes shape so that such a resistance force fades when the temperature of the insertion portion 2 is heated to a predetermined temperature range that exceeds the predetermined temperature.

Figure 7:
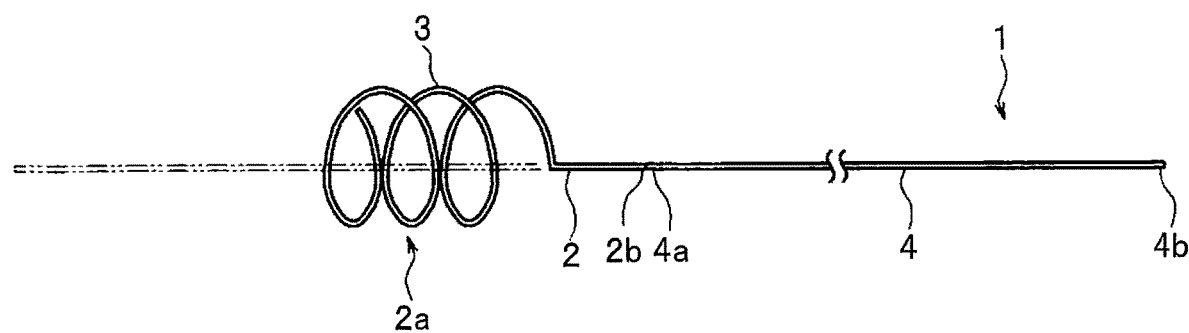
FIG. 7 is a view illustrating a first modification of an insertion portion and the locking portion of the first embodiment.

FIG. 7 is a view illustrating a first modification of the insertion portion 2 and the locking portion 3. As shown in FIG. 7, in a case where the temperature of the locking portion 3 of the present embodiment is less than or equal to the predetermined temperature, the distal end portion 2a of the insertion portion 2 that is made of a linear shape-memory alloy has a shape which is wound in a coil shape. In a case where the locking portion 3 is heated to the predetermined temperature range that exceeds the predetermined temperature, as shown by a chain double-dashed line in FIG. 7, the locking portion 3 changes shape to become a rectilinear shape.

Figure 8:
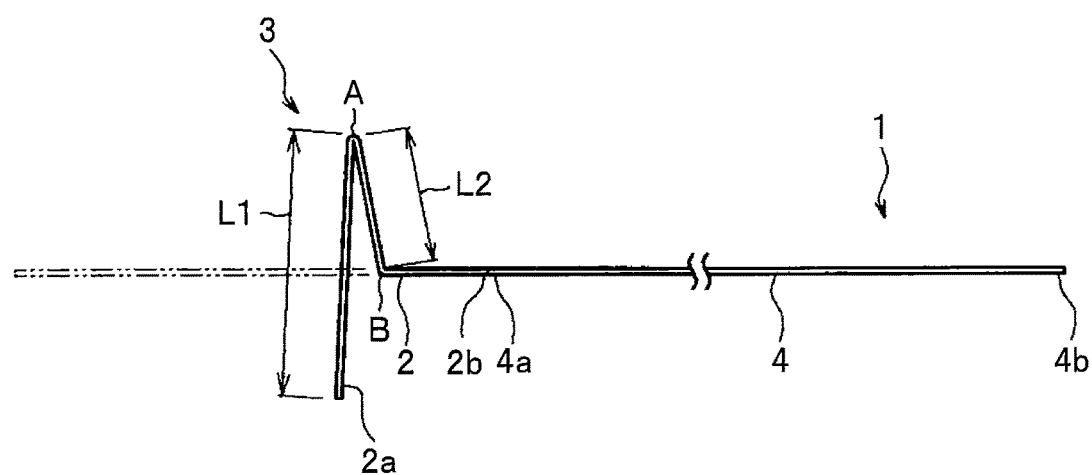
FIG. 8 is a view illustrating a second modification of the insertion portion and the locking portion of the first embodiment.

FIG. 8 is a view that illustrates a second modification of the insertion portion 2 and the locking portion 3. As shown in FIG. 8, in a case where the temperature of the locking portion 3 of the present embodiment is less than or equal to the predetermined temperature, the distal end portion 2a of the insertion portion 2 that is made of a linear shape-memory alloy has a shape which is bent in substantially a T-shape. Specifically, the locking portion 3 has a shape which turns back at an angle of approximately 180 degrees at a point A that is a distance of a predetermined length L1 on the proximal end side from the distal end of the insertion portion 2, and is further bent at an angle of approximately 90 degrees at a point B that is a distance of a length L2 which is shorter than the length L1 on the proximal end side from the point A. In a case where the locking portion 3 is heated to the predetermined temperature range that exceeds the predetermined temperature, as shown by a chain double-dashed line in FIG. 8, the locking portion 3 changes shape into a rectilinear shape.

Figure 9:
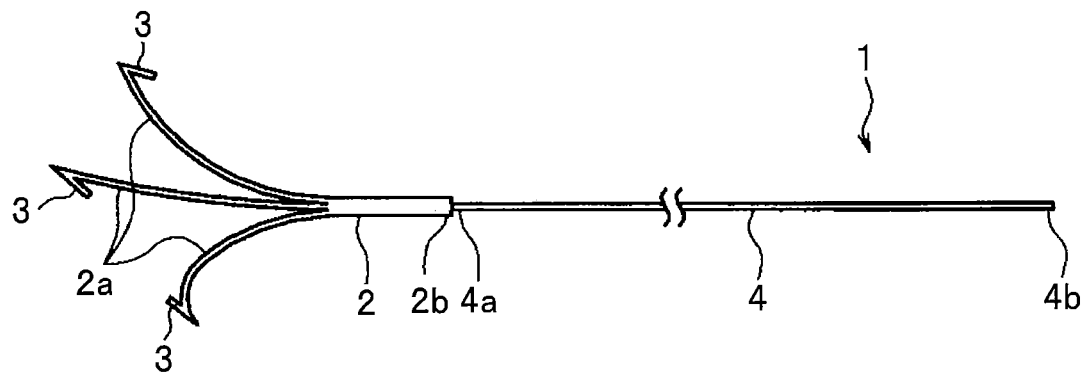
FIG. 9 is a view illustrating a third modification of the insertion portion and the locking portion of the first embodiment.

FIG. 9 is a view that illustrates a third modification of the insertion portion 2 and the locking portion 3. As shown in FIG. 9, the distal end portion 2a of the insertion portion 2 of the present embodiment is divided into a plurality of portions, and the locking portion 3 is provided on each of the distal end portions 2a.

Figure 10:
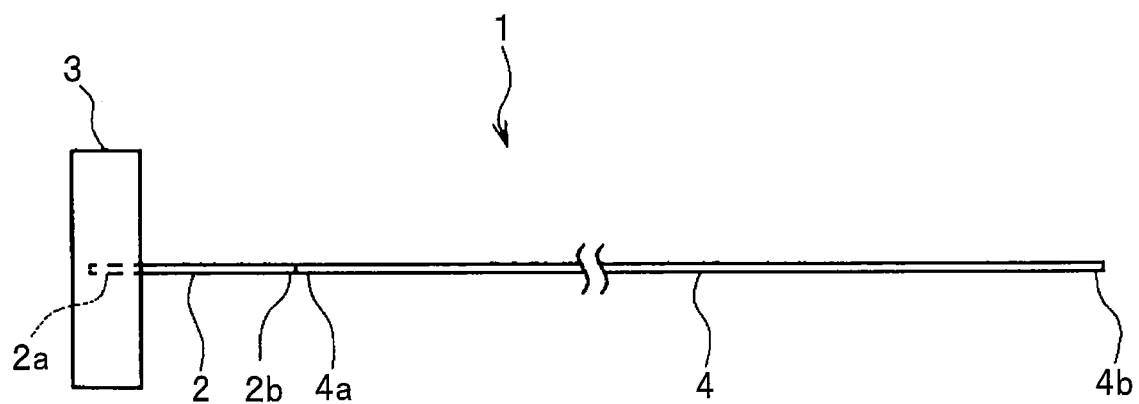
FIG. 10 is a view illustrating a fourth modification of the insertion portion and the locking portion.

FIG. 10 is a view that illustrates a fourth modification of the insertion portion 2 and the locking portion 3. In the present embodiment, the insertion portion 2 is a member having a linear shape. The locking portion 3 is a member that is fixed to the distal end portion 2a of the insertion portion 2, and has an outer shape that protrudes to the sides of the distal end portion 2a when the temperature is less than or equal to the predetermined temperature.

The locking portion 3 of the present embodiment is constituted by a material that melts or softens in a case where the material is heated to a predetermined temperature range that exceeds a predetermined temperature. The material constituting the locking portion 3 is, for example, beeswax, bone wax or paraffin. In the present embodiment, in a case where the locking portion 3 is heated to the predetermined temperature range that exceeds the predetermined temperature and a force in a withdrawing direction is applied to the insertion portion 2, the locking portion 3 changes shape in accordance with the force, and consequently the engagement between the locking portion 3 and the tissue 10 is released.

Even in the case of the modifications illustrated in FIG. 7 to FIG. 10, as described above, when performing thermal therapy, by using the heat monitoring instrument 1 the user can easily and reliably know the state of an increase in the temperature of tissue at a desired location during performance of the thermal therapy. Further, because the heat monitoring instrument 1 according to these modifications has a simple structure in which the locking portion 3 is fixed to the distal end portion of a member having a linear shape, the heat monitoring instrument 1 can be manufactured at a low cost.

Second Embodiment

A second embodiment of the present invention will be described hereunder. Hereunder, only differences with respect to the first embodiment are described, and components that are the same as in the first embodiment are denoted by the same reference numerals and a description of such components is omitted as appropriate.

Figure 11:
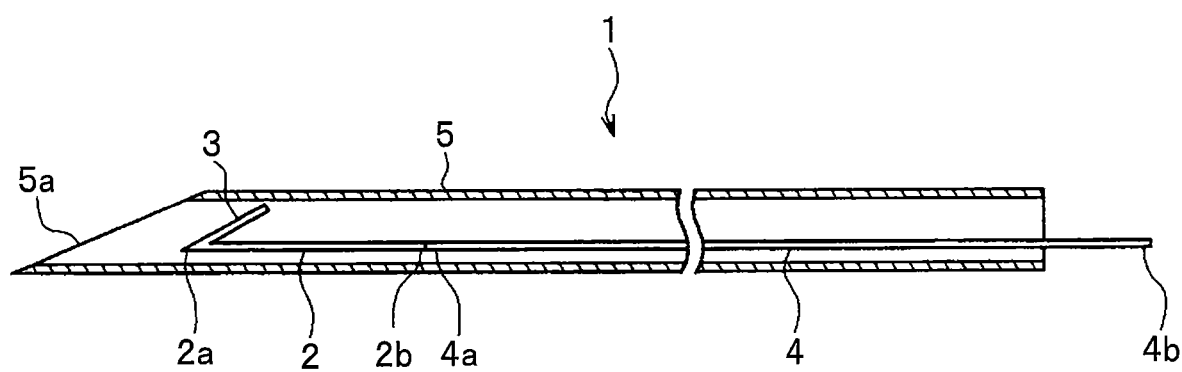
FIG. 11 is a view illustrating a configuration of a heat monitoring instrument according to a second embodiment.

As shown in FIG. 11, the heat monitoring instrument 1 of the present embodiment differs from the first embodiment in that the heat monitoring instrument 1 of the present embodiment includes a cylindrical member 5.

The cylindrical member 5 is a hollow tubular member, and it is possible to insert the insertion portion 2, the locking portion 3 and the linear member 4 through the inside thereof. As one example according to the present embodiment, the cylindrical member 5 is a needle tube having a shape that is diagonally cut in the longitudinal direction to make it easy for the distal end portion 5a to pierce the tissue 10 of the organism. The proximal end portion 4b of the linear member 4 extends to the outside from the proximal end portion of the cylindrical member 5. Note that the distal end portion 5a of the cylindrical member 5 may also be a shape that is cut at a face that is perpendicular to the longitudinal direction.

In the present embodiment, the form of the insertion portion 2 and the locking portion 3 is not limited to a form in which the locking portion 3 is a hook shape as shown in the drawing, and may be a form of a modification described referring to FIG. 7 to FIG. 10 in the first embodiment.

Figure 12:
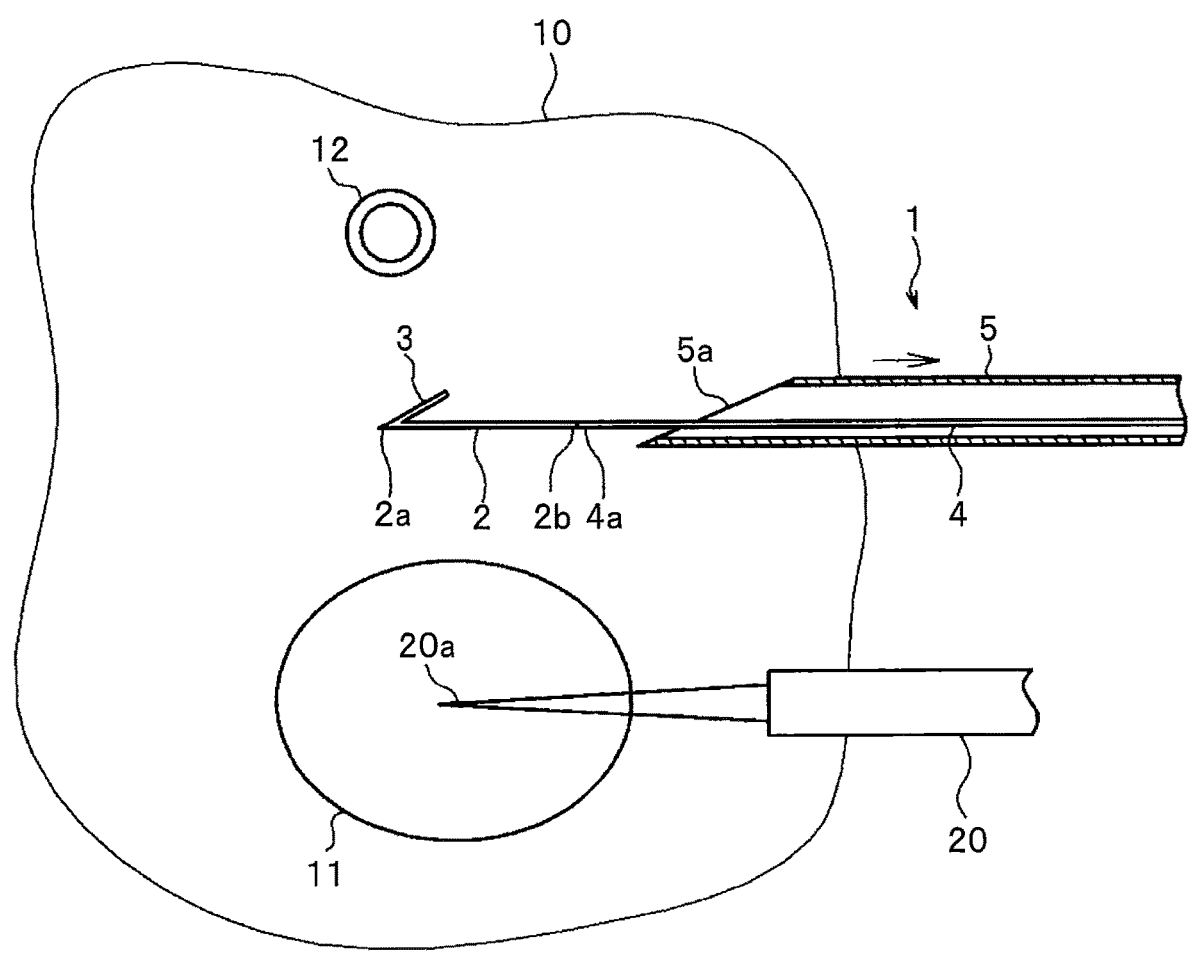
FIG. 12 is a schematic diagram illustrating a state in which the heat monitoring instrument of the second embodiment is inserted into tissue.

When using the heat monitoring instrument 1 of the present embodiment, the cylindrical member 5 is pierced into the tissue 10 in a state in which the insertion portion 2 and locking portion 3 are contained inside the cylindrical member 5, and thereafter, as shown in FIG. 12, the insertion portion 2 and the locking portion 3 are disposed inside the tissue 10 by moving the cylindrical member 5 to the proximal end side relative to the insertion portion 2, the locking portion 3 and the linear member 4. Note that, the cylindrical member 5 may be of a form that moves relatively by the amount of only a predetermined distance towards the proximal end side from the distal end portion 3a of the locking portion 3, or may be of a form that moves relatively as far as the proximal end portion 4b of the linear member 4 so that the insertion portion 2, the locking portion 3 and the linear member 4 come out from the inside of the cylindrical member 5.

Thus, according to the present embodiment, because the insertion portion 2 and the locking portion 3 are inserted into the tissue 10 using the cylindrical member 5, an operation to dispose the insertion portion 2 and the locking portion 3 at a predetermined location of the tissue 10 is facilitated.

For example, in a case where the shape of the locking portion 3 is the coil shape shown in FIG. 7 or the T-shape shown in FIG. 8, because there is a large amount of resistance when the insertion portion 2 is inserted into the tissue 10 in a state in which the locking portion 3 is exposed, insertion of the insertion portion 2 as far as a deep position is difficult. According to the present embodiment, as shown in FIG. 13 and FIG. 14, by housing the locking portion 3 that is a T-shape or a coil shape inside the cylindrical member 5, it is possible to easily insert the insertion portion 2 and the locking portion 3 as far as a predetermined location in the tissue 10.

Figure 13:
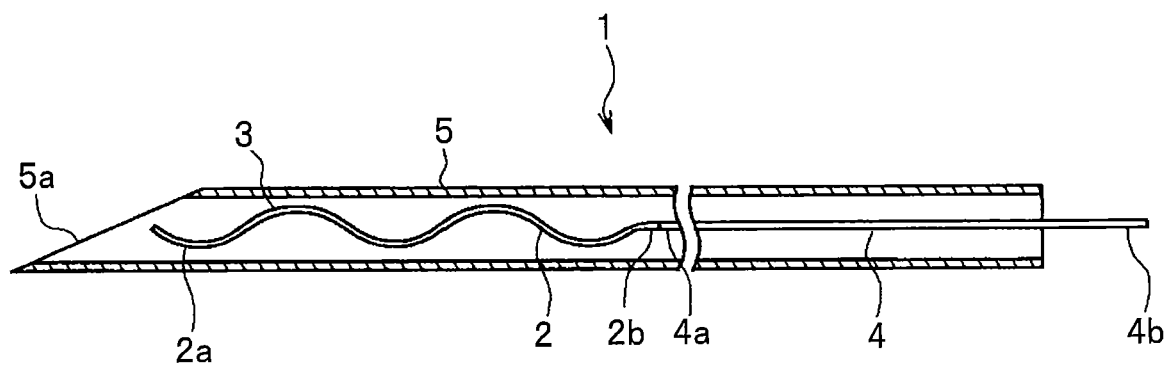
FIG. 13 is a view illustrating a state in which a T-shaped locking portion is housed inside a cylindrical member.
Figure 14:
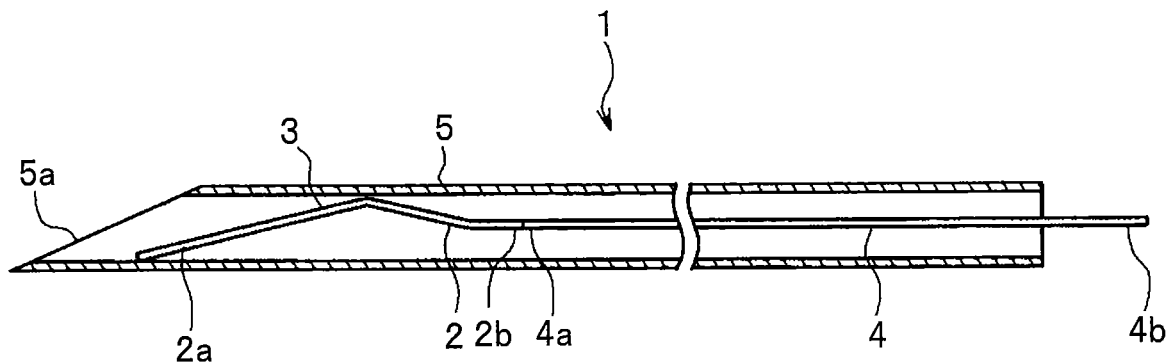
FIG. 14 is a view illustrating a state in which a coil-shaped locking portion is housed inside a cylindrical member.

In the embodiment shown in FIG. 13 and in FIG. 14, in a state in which the locking portion 3 is contained inside the cylindrical member 5, the locking portion 3 elastically changes shape to a shape that fits within the inner diameter of the cylindrical member 5. The locking portion 3 expands based on the elasticity thereof when the locking portion 3 is brought outside of the cylindrical member 5 inside the tissue 10, and returns to a shape that engages with the tissue 6 as shown in FIG. 7 and FIG. 8.

In the present embodiment also, similarly to the first embodiment, when performing thermal therapy, by using the heat monitoring instrument 1 the user can easily and reliably know the state of an increase in the temperature of tissue at a desired location during performance of the thermal therapy. Further, because the heat monitoring instrument 1 has a simple structure, the heat monitoring instrument 1 can be manufactured at a low cost.

Note that, as long as the linear member 4 is of a form that does not easily buckle with respect to a compressive force in the longitudinal direction, as in the case of, for example, a metal wire, an operation to move the cylindrical member 5 to the proximal end side relative to the insertion portion 2, the locking portion 3 and the linear member 4 inside the tissue 10 can be easily performed by merely pulling the cylindrical member 5 in the proximal end direction while keeping the linear member 4 fixed.

Figure 15:
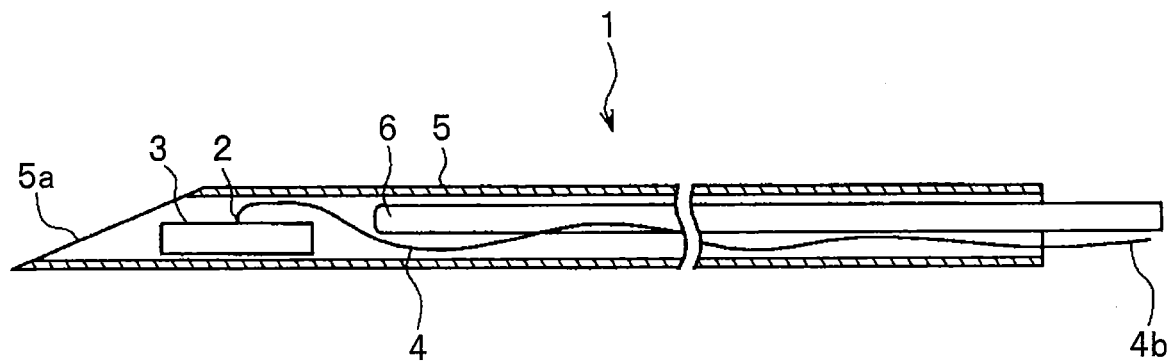
FIG. 15 is a view illustrating the heat monitoring instrument of the second embodiment that includes a pressing member.
Figure 16:
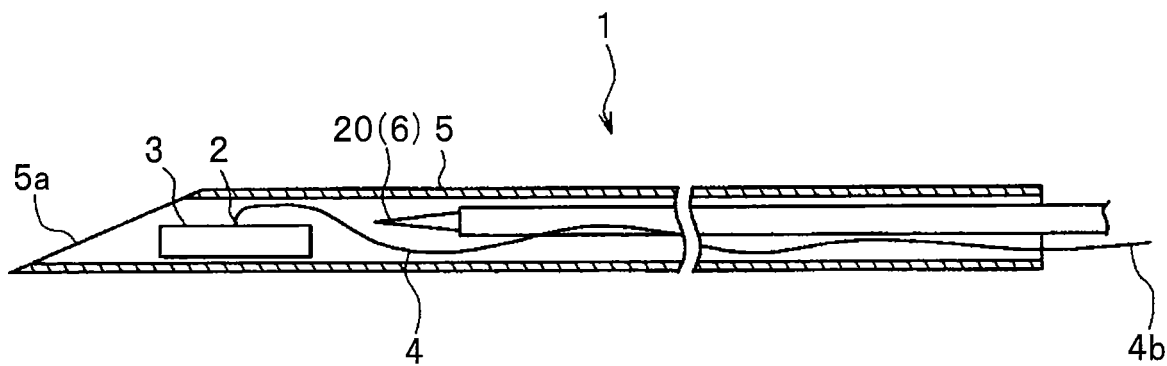
FIG. 16 is a view illustrating the heat monitoring instrument of the second embodiment in which a thermal therapy instrument is configured as a pressing member.

However, in a case where the linear member 4 has a flexible form such as string, an operation is required to push out the insertion portion 2 and the locking portion 3 relatively from inside the cylindrical member 5 to the distal end side. Therefore, in a case where the linear member 4 has a flexible form such as string, as shown in FIG. 15, a pressing member 6 is arranged inside the cylindrical member 5. The pressing member 6 is a member that is longer than the cylindrical member 5, and has an outer diameter that is smaller than the inner diameter of the cylindrical member 5. The pressing member 6 has stiffness such that the pressing member 6 does not buckle even if a force of an amount required for pushing out the insertion portion 2 and the locking portion 3 from inside the cylindrical member 5 into the tissue 10 is applied in the axial direction. Note that, as shown in FIG. 16, the thermal therapy instrument 20 that is inserted through the inside of the cylindrical member 5 may also be used as the pressing member 6.

Although in the present embodiment that is described above the cylindrical member 5 has the form of a needle tube, the form of the cylindrical member 5 is not limited thereto.

Figure 17:
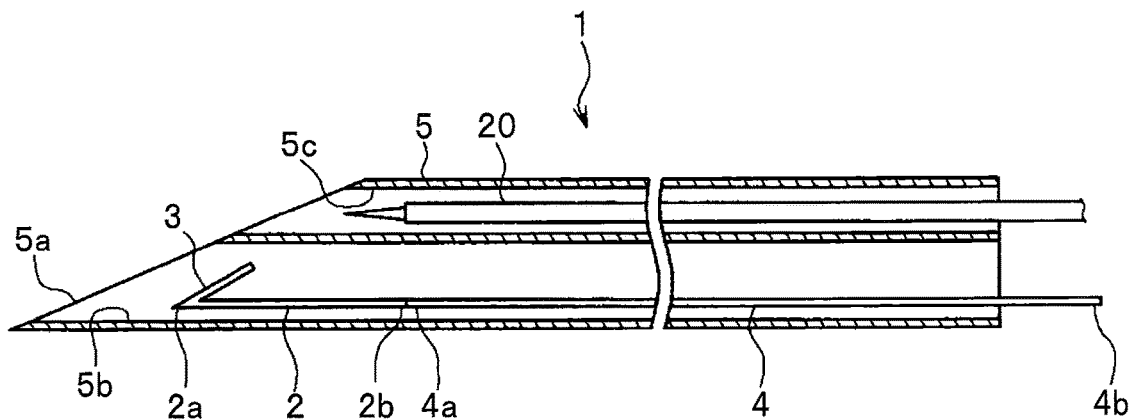
FIG. 17 is a view illustrating a first modification of the cylindrical member of the second embodiment.

For example, as shown as a first modification in FIG. 17, the cylindrical member 5 may also be of a form that includes a plurality of conduits. According to the present modification that is illustrated in FIG. 17, the cylindrical member 5 includes two conduits 5b and 5c. The heat monitoring instrument 1 is inserted through one of the conduits, i.e. the conduit 5b, and the thermal therapy instrument 20 is inserted through the other conduit, i.e. the conduit 5c.

Figure 18:
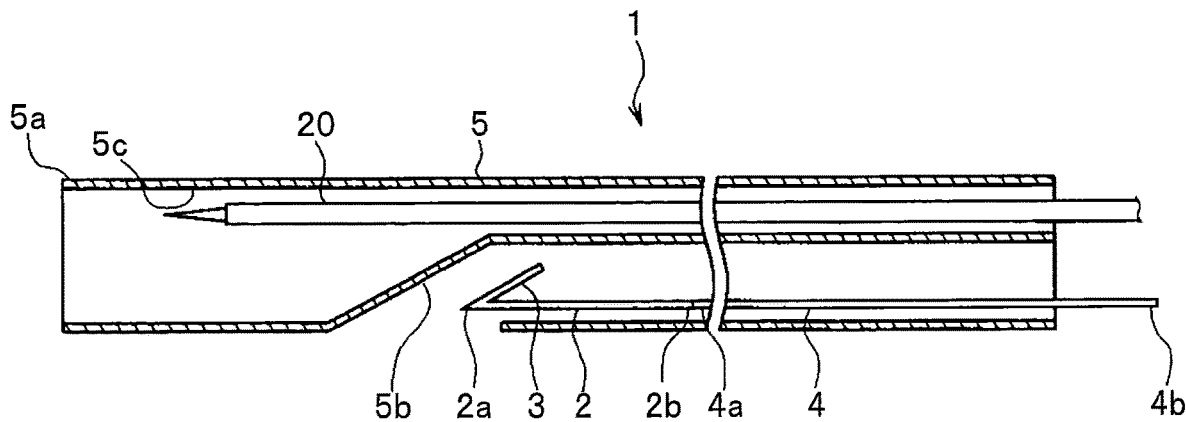
FIG. 18 is a view illustrating a second modification of the cylindrical member of the second embodiment.

As shown as a second modification in FIG. 18, in a case where the cylindrical member 5 has a plurality of conduits, the opening portions on the distal end side of the respective conduits may be provided apart from each other in the longitudinal direction of the cylindrical member 5. In the present modification illustrated in FIG. 18, the cylindrical member 5 has a conduit 5b through which the heat monitoring instrument 1 is inserted, and a conduit 5c through which the thermal therapy instrument 20 is inserted. The conduit 5c opens at the distal end of the cylindrical member 5, and the conduit 5b opens at a position on the proximal end side that is separated from the distal end of the cylindrical member 5 by a predetermined distance.

Figure 19:
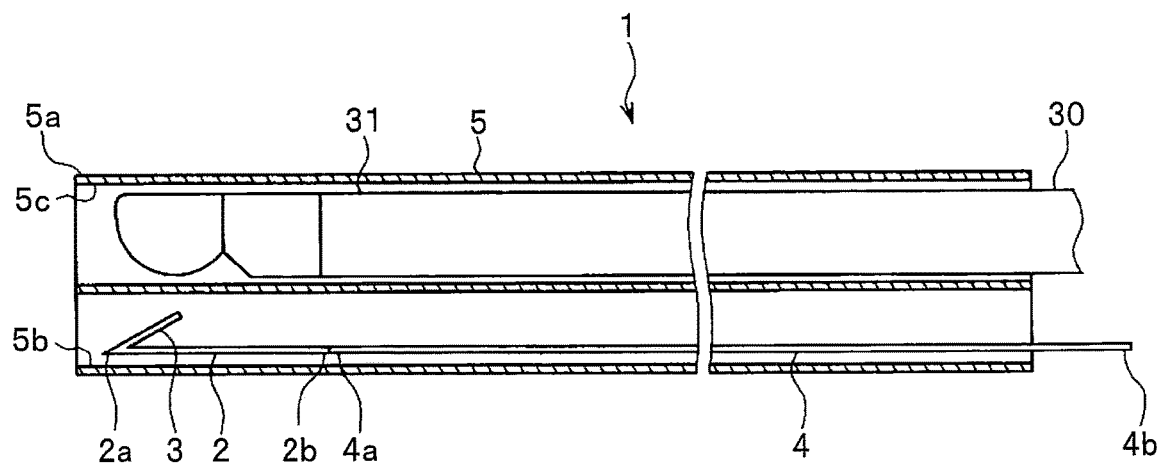
FIG. 19 is a view illustrating a third modification of the cylindrical member of the second embodiment.

Further, for example, as shown as a third modification in FIG. 19, the cylindrical member 5 may be of a form that includes two conduits 5b and 5c, in which the heat monitoring instrument 1 is inserted through the conduit 5b, and the insertion portion 31 of the ultrasound endoscope 30 is inserted through the conduit 5c. A cylindrical member through which the ultrasound endoscope 30 is inserted in this manner is referred to as an "overtube" or the like.

Even in the case of the modifications illustrated in FIG. 17 to FIG. 19, as described above, when performing thermal therapy, by using the heat monitoring instrument 1 the user can easily and reliably know the state of an increase in the temperature of tissue at a desired location during performance of the thermal therapy. Further, because the heat monitoring instrument 1 according to these modifications has a simple structure, the heat monitoring instrument 1 can be manufactured at a low cost.

Third Embodiment

A third embodiment of the present invention will be described hereunder. Hereunder, only differences with respect to the first and second embodiments are described, and components that are the same as in the first and second embodiments are denoted by the same reference numerals and a description of such components is omitted as appropriate.

In the foregoing first and second embodiments, in a case where the insertion portion 2 of the heat monitoring instrument 1 is inserted inside the tissue 10 and the temperature is less than or equal to the predetermined temperature, the locking portion 3 engages with the surrounding tissue 10. In contrast, according to the present embodiment, in a case where the insertion portion 2 of the heat monitoring instrument 1 is inserted inside the cylindrical member 5 and the temperature is less than or equal to the predetermined temperature, the locking portion 3 engages with the cylindrical member 5.

Figure 20:
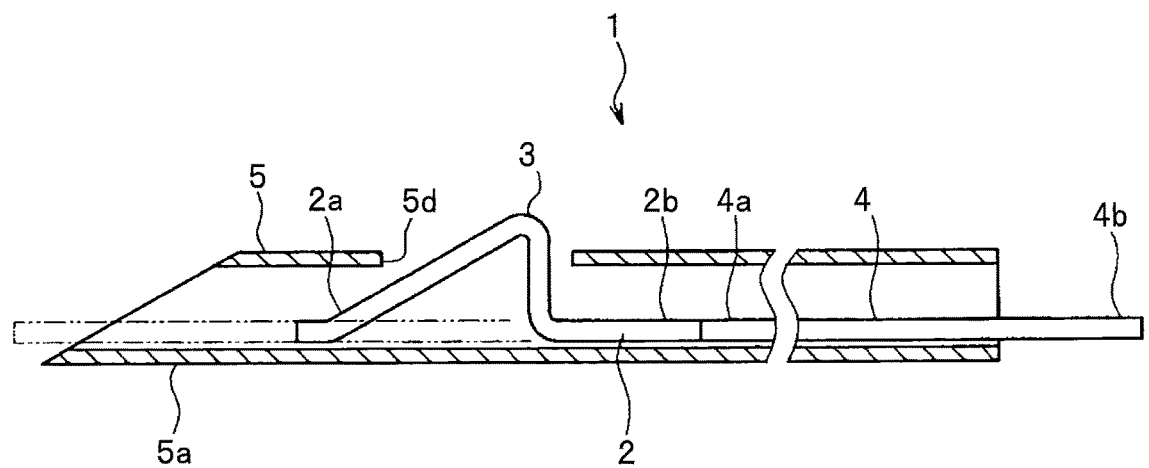
FIG. 20 is a view illustrating a heat monitoring instrument of a third embodiment.

As shown in FIG. 20, the heat monitoring instrument 1 includes the cylindrical member 5, and the insertion portion 2 and linear member 4 that are inserted through the inside of the cylindrical member 5. The locking portion 3 is provided at the distal end portion 2a of the insertion portion 2.

As one example according to the present embodiment, the cylindrical member 5 is a needle tube that can be pierced into the tissue 10. A through-hole 5d is formed in the wall face in the vicinity of the distal end portion 5a of the cylindrical member 5.

Similarly to the first and second embodiments, the linear member 4 is an elongated member having a linear shape that is made of metal, synthetic resin or the like.

The insertion portion 2 is composed of a member having a linear shape. The locking portion 3 is provided at the distal end portion 2a that is one end portion of the insertion portion 2. The proximal end portion 2b that is the other end portion of the insertion portion 2 is coupled to the distal end portion 4a of the linear member 4. The insertion portion 2 of the present embodiment is made of a shape-memory alloy that changes shape into a rectilinear shape when heated to a predetermined temperature range that exceeds a predetermined temperature. Note that, the linear member 4 and the insertion portion 2 may also be formed integrally by a single member.

The locking portion 3 is formed by bending the distal end portion 2a of the insertion portion 2 that is made of a linear shape-memory alloy into a hook shape in a state in which the temperature of the insertion portion 2 is less than or equal to the predetermined temperature. The locking portion 3 protrudes to the outside of the cylindrical member 5 through the through-hole 5d formed in the wall face of the cylindrical member 5. Hence, in a case where the temperature of the locking portion 3 is less than or equal to a predetermined temperature, the locking portion 3 engages with the cylindrical member 5.

Further, in a state in which the locking portion 3 is engaged in the through-hole 5d of the cylindrical member 5, the proximal end portion 4b of the linear member 4 extends to the outside from the proximal end of the cylindrical member 5.

If the locking portion 3 is heated from the state in which the temperature thereof is the predetermined temperature up to the predetermined temperature range that exceeds the predetermined temperature, as shown by a chain double-dashed line in FIG. 20, the locking portion 3 changes shape to become a rectilinear shape. Hence, in a case where the locking portion 3 is heated up to the predetermined temperature range from the state in which the temperature thereof is less than or equal to the predetermined temperature, the locking portion 3 changes shape to become a rectilinear shape to thereby release the engagement with the cylindrical member 5.

Figure 21:
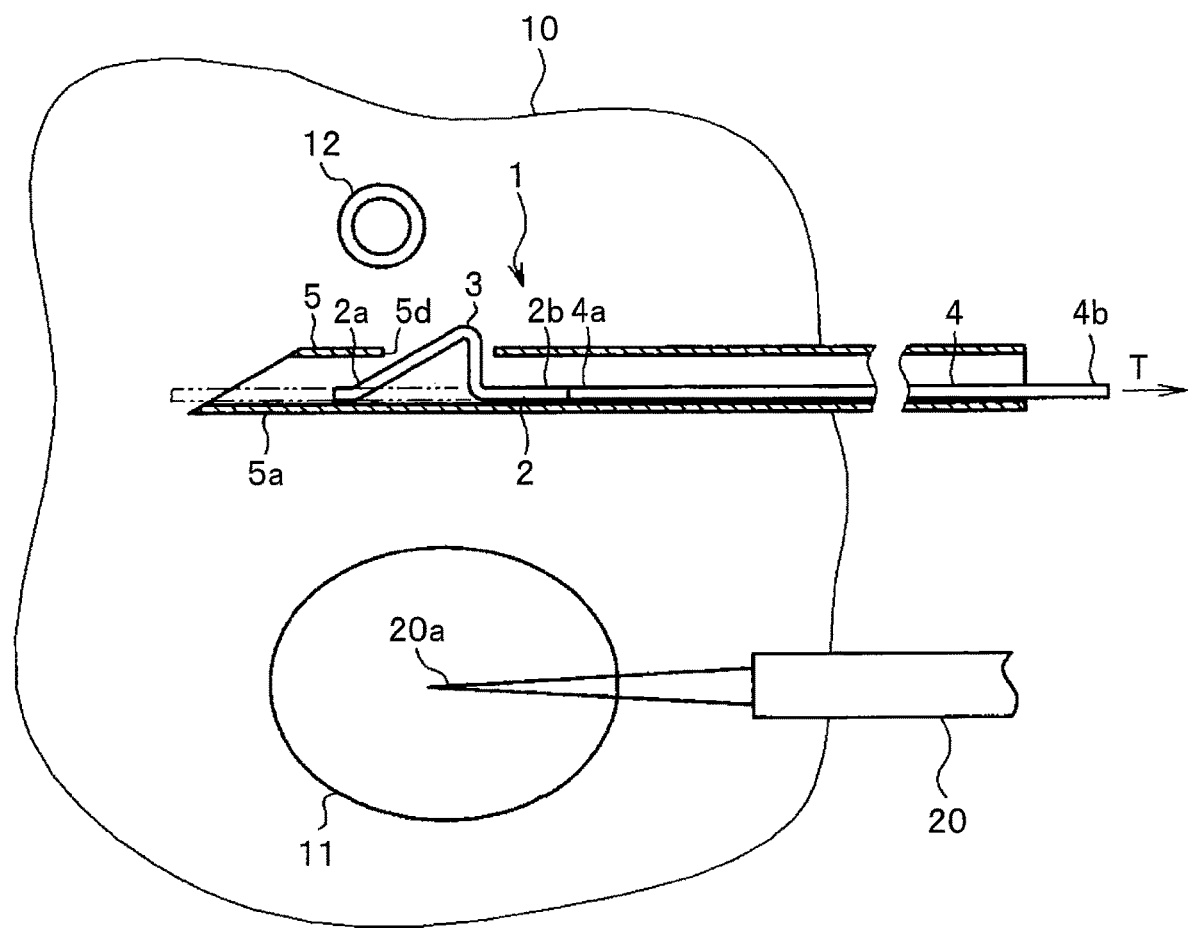
FIG. 21 is a schematic diagram illustrating a state in which the heat monitoring instrument of the third embodiment is inserted into tissue.

When using the heat monitoring instrument 1 of the present embodiment when performing thermal therapy, as shown in FIG. 21, the cylindrical member 5 of the heat monitoring instrument 1 is inserted into the tissue 10, and the locking portion 3 is disposed at a location at which it is desired to detect the state of a change in temperature inside the tissue 10. As one example according to the present embodiment, the location at which the locking portion 3 is disposed so as to detect the state of a change in temperature inside the tissue 10 is between the distal end portion 20a of the thermal therapy instrument 20 and a blood vessel 12. Note that, the location at which the locking portion 3 is disposed is not limited thereto, and may be a boundary portion between the target site 11 that is the tumor cells and the healthy cells, or may be inside the target site 11.

The insertion path of the cylindrical member 5 into the tissue 10 may be a path that passes through the skin from outside the body of the subject, or a path that passes from inside the digestive tract of the subject through a tubular wall of the digestive tract, or a path that passes from inside a body cavity through an outer wall of an internal organ having the tissue 10. An operation to insert the cylindrical member 5 to a predetermined position inside the tissue 10 is performed, for example, under observation by means of an ultrasound diagnostic apparatus such as the ultrasound endoscope 30. Similarly to the first and second embodiments, a tensile force T is applied by means of a finger of the user or by a pulling apparatus of some kind (for example, a weight 7) to the linear member 4.

When the thermal therapy instrument 20 is operated and the temperature of the locking portion 3 is heated to the predetermined temperature range that exceeds the predetermined temperature as a result of the heat of the thermal therapy being transmitted to the surrounding area, the locking portion 3 changes shape and the engagement between the locking portion 3 and the cylindrical member 5 is released and the insertion portion 2 drops out from the cylindrical member 5. By confirming the withdrawal of the insertion portion 2 from the cylindrical member 5, the user can determine that the tissue 10 at the location at which the locking portion 3 had been disposed is heated to the predetermined temperature range.

As described above, according to the present embodiment, when performing thermal therapy, by using the heat monitoring instrument 1 the user can easily and reliably know the state of an increase in the temperature of tissue at a desired location during performance of the thermal therapy. Further, because the heat monitoring instrument 1 of the present embodiment has a simple structure, the heat monitoring instrument 1 can be manufactured at a low cost.

Fourth Embodiment

A fourth embodiment of the present invention will be described hereunder. Hereunder, only differences with respect to the first to third embodiments are described, and components that are the same as in the first to third embodiments are denoted by the same reference numerals and a description of such components is omitted as appropriate.

Figure 22:
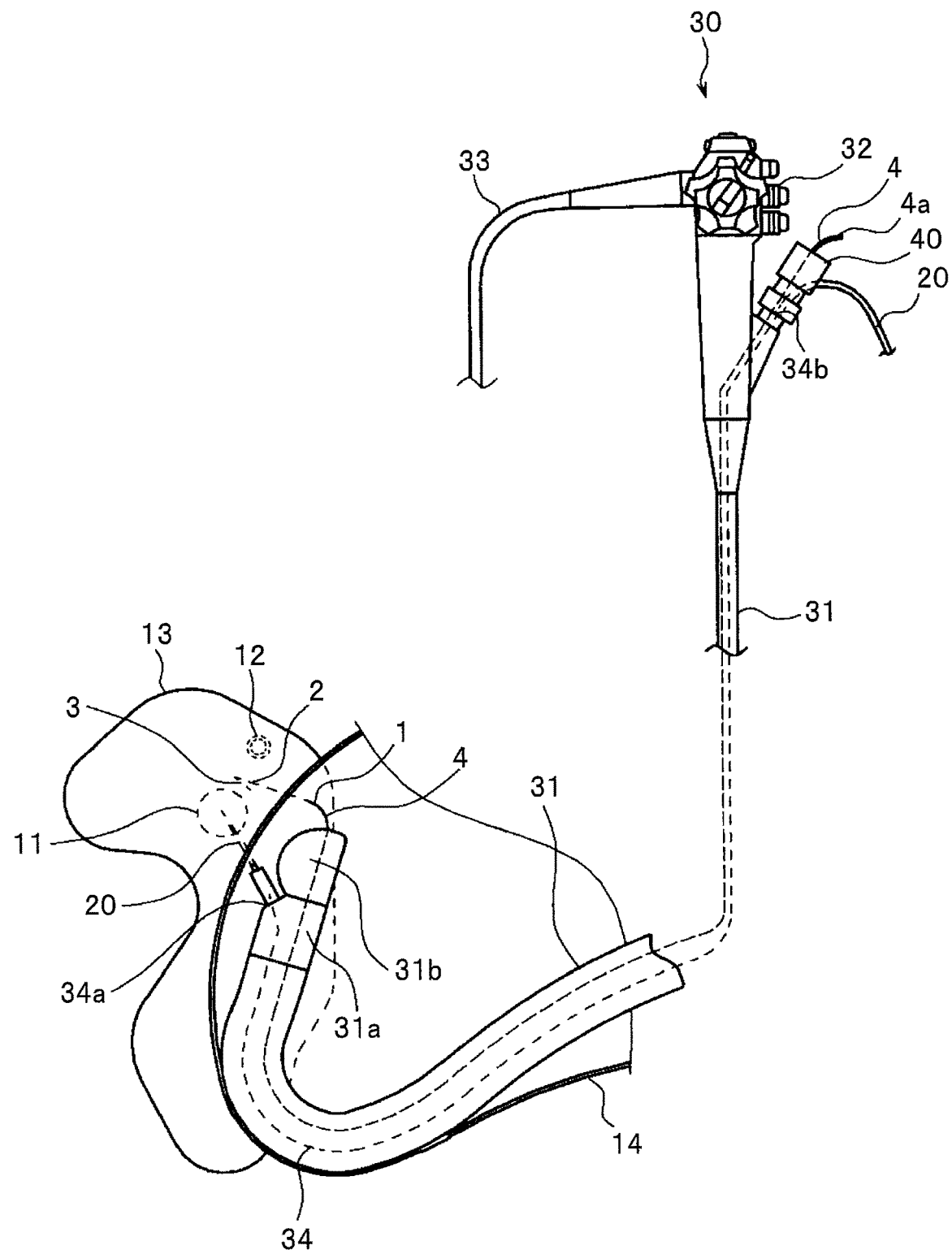
FIG. 22 is a view illustrating a heat monitoring instrument and a pulling apparatus of a fourth embodiment.

In the present embodiment, a pulling apparatus 40 that applies the tensile force T to the linear member 4 when using the heat monitoring instrument 1 described in the first to third embodiments when performing thermal therapy will be described. As one example according to the present embodiment, as shown in FIG. 22, it is assumed that thermal therapy is performed on the subject using the ultrasound endoscope 30 and the thermal therapy instrument 20.

The proximal end portion 4b of the linear member 4 of the heat monitoring instrument 1 extends from the proximal-end-side opening portion 34b through the treatment instrument channel 34 that is a conduit provided in the ultrasound endoscope 30. The pulling apparatus 40 is fixed to the proximal-end-side opening portion 34b of the treatment instrument channel 34 of the ultrasound endoscope 30.

Figure 23:
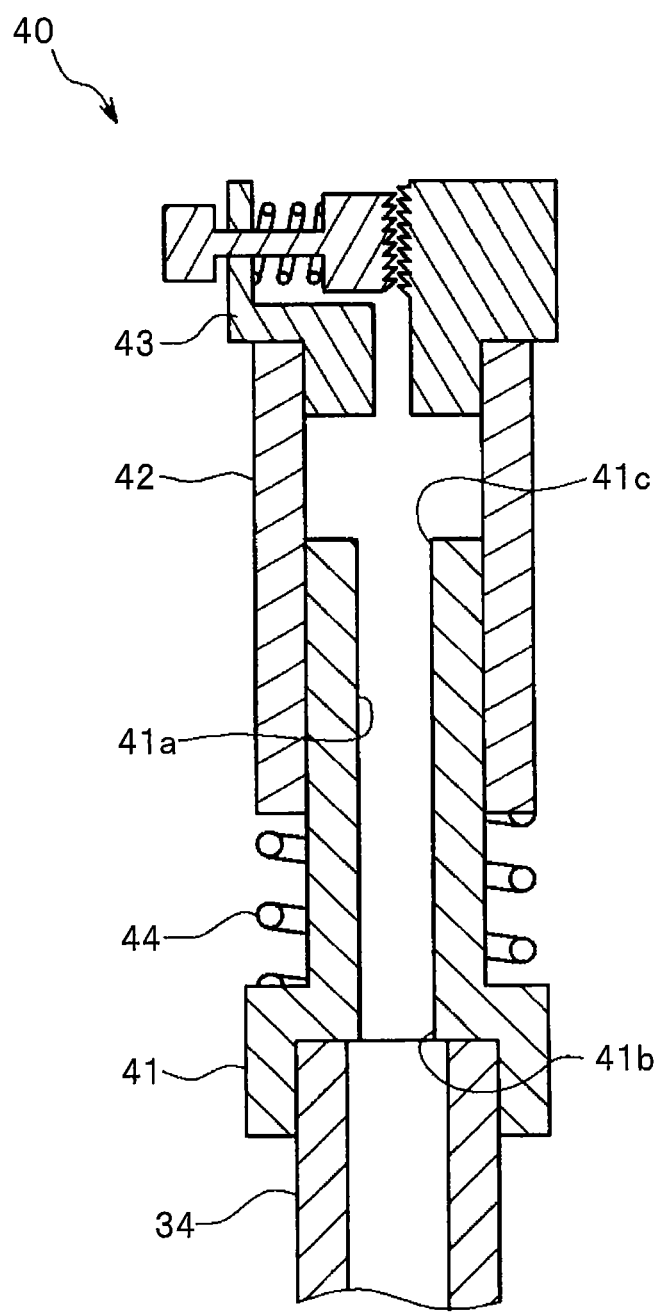
FIG. 23 is a cross-sectional diagram illustrating the configuration of the pulling apparatus of the fourth embodiment.

As shown in FIG. 23, the pulling apparatus 40 has a configuration that includes a base portion 41, a slider 42, a holding portion 43 and an urging member 44.

The base portion 41 is a member that is fixed to the proximal-end-side opening portion 34b. A through-hole 41a is formed in the base portion 41. In a state in which the base portion 41 is fixed to the proximal-end-side opening portion 34b, an end 41b of the through-hole 41a faces the proximalend-side opening portion 34b. Accordingly, in a state in which the base portion 41 is fixed to the proximal-end-side opening portion 34b, the through-hole 41a and the treatment instrument channel 34 are connected.

The slider 42 is a member that moves relatively with respect to the base portion 41. The slider 42 moves relatively with respect to the base portion 41 along the central axis of the through-hole 41a. The holding portion 43 is fixed to the slider 42.

The holding portion 43 is a member that moves relatively with respect to the base portion 41 along the central axis of the through-hole 41a together with the slider 42. The holding portion 43 is arranged facing another end 41c of the through-hole 41a that is provided in the base portion 41. That is, the holding portion 43 moves forward/rearward along the central axis of the through-hole 41a so that a distance between the holding portion 43 and the other end 41c of the through-hole 41a changes.

The holding portion 43 has a structure that holds the proximal end portion 4b of the linear member 4. Holding of the proximal end portion 4b of the linear member 4 by the holding portion 43 can be released by an operation of the user. According to the present embodiment that is illustrated in the drawings, as one example the holding portion 43 has a configuration that pinches the proximal end portion 4b of the linear member 4 from the sides like a clip.

The urging member 44 is a member made of a spring or the like that urges the slider 42 in a direction away from the proximal-end-side opening portion 34b. In other words, the urging member 44 urges the holding portion 43 in a direction away from the other end 41c of the through-hole 41a along the central axis of the through-hole 41a.

Figure 24:
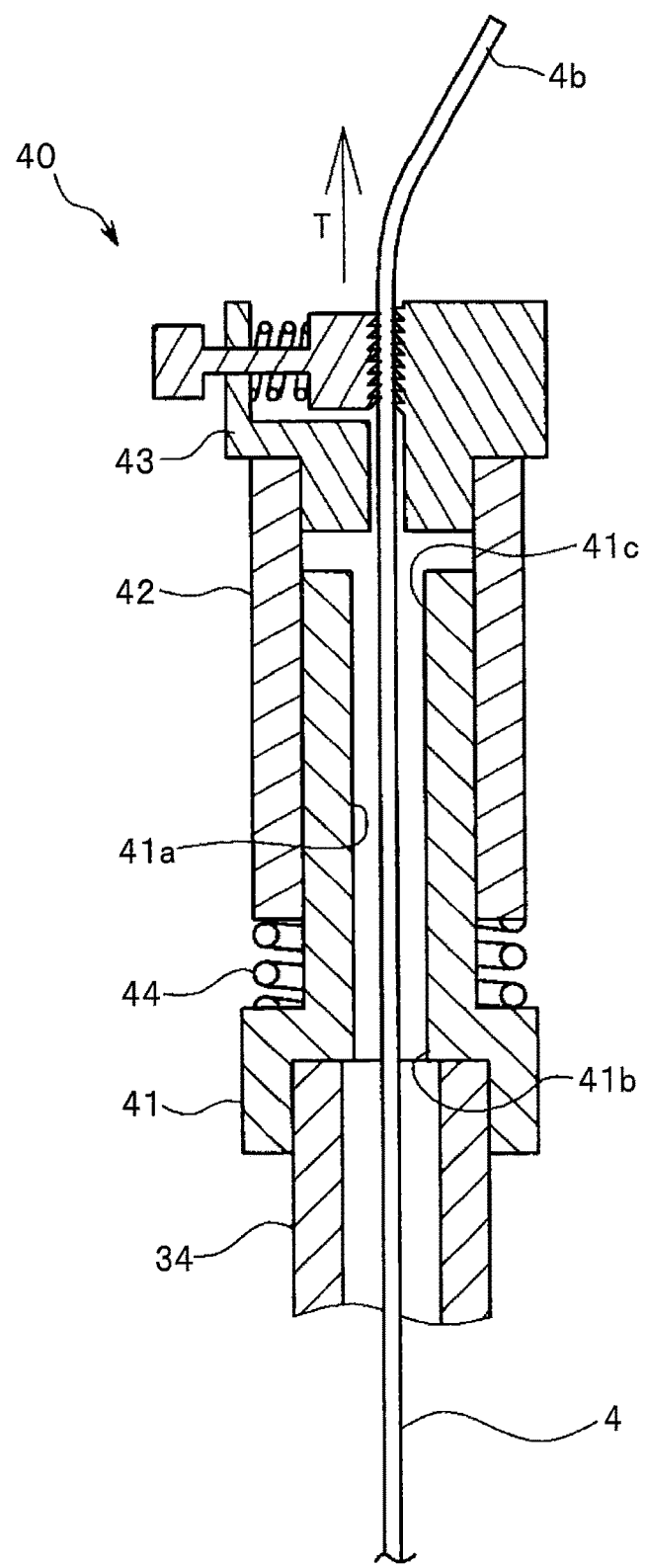
FIG. 24 is a view illustrating a state in which a proximal end portion of a linear member is held by the pulling apparatus of the fourth embodiment.

When performing thermal therapy, as shown in FIG. 24, in a state in which the holding portion 43 is brought near to the other end of the other end 41c of the through-hole 41a against the urging force of the urging member 44, the proximal end portion 4b of the linear member 4 that extends from the proximal-end-side opening portion 34b is held by the holding portion 43. By this means, since the urging force of the urging member 44 is transmitted to the linear member 4, the tensile force T is applied to the linear member 4.

Figure 25:
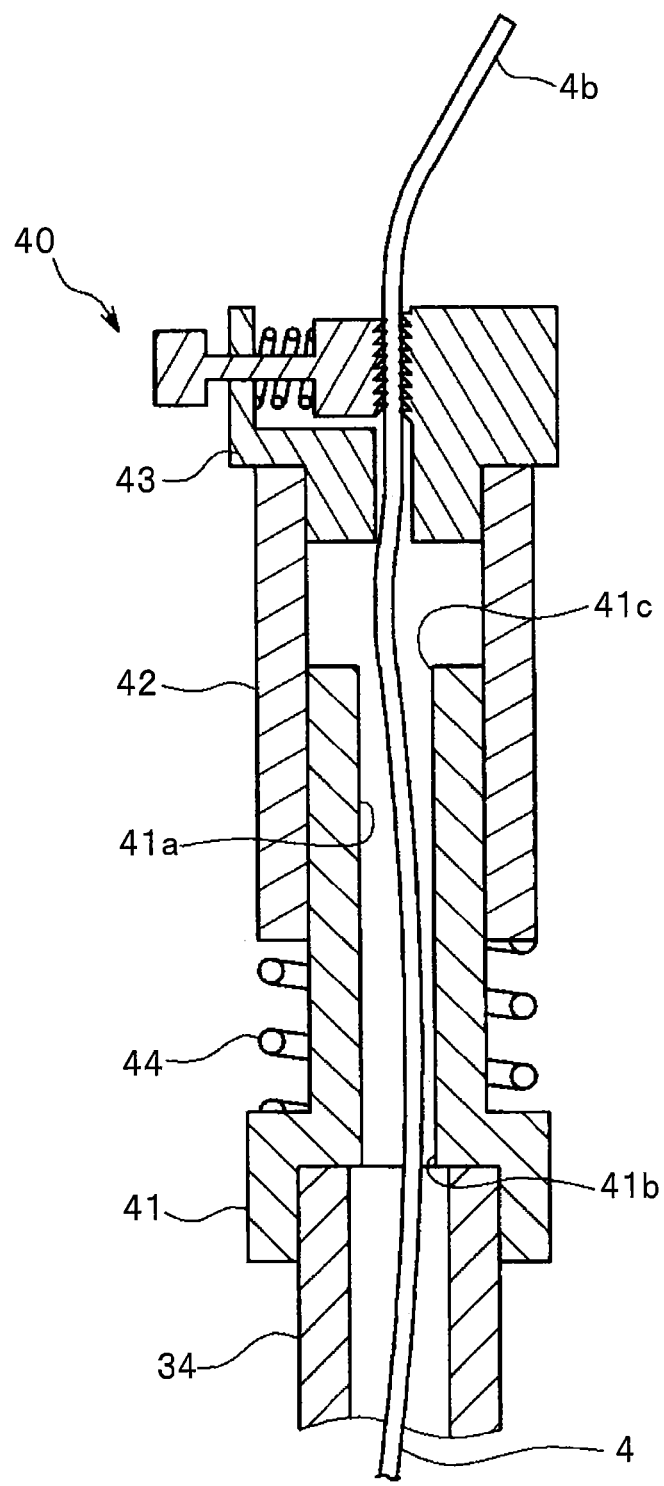
FIG. 25 is a view illustrating a state in which, in the fourth embodiment, the insertion portion of the linear member is withdrawn from tissue or a cylindrical member.
Figure 26:
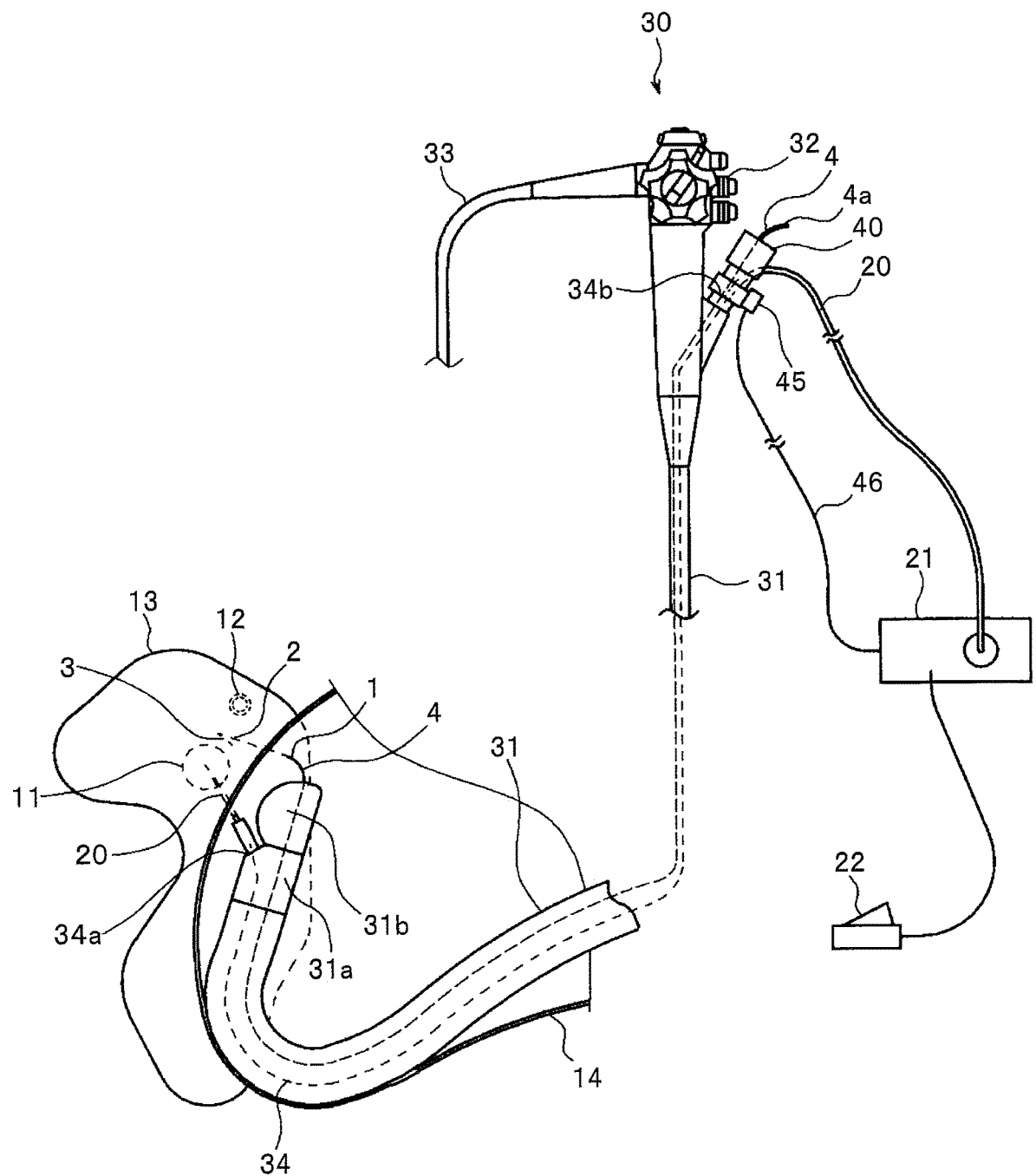
FIG. 26 is a view illustrating a heat monitoring instrument and a pulling apparatus of a fifth embodiment.

Further, when heating is performed such that the temperature of the locking portion 3 of the heat monitoring instrument 1 reaches the predetermined temperature range that exceeds the predetermined temperature, because the engagement between the locking portion 3 and the tissue 10 or the cylindrical member 5 is released, the insertion portion 2 is caused to withdraw from inside the tissue 10 or inside the cylindrical member 5 by the urging force of the urging member 44. At such time, as shown in FIG. 25, the holding portion 43 is moved in a direction away from the other end 41c of the through-hole 41a. Therefore, apart from observation using an optical image and an ultrasound image using the ultrasound endoscope 30, the user can confirm that the insertion portion 2 has been withdrawn from the tissue 10 or the cylindrical member 5 by looking at the movement of the holding portion 43.

Thus, according to the present embodiment, similarly to the above described first to third embodiments, when performing thermal therapy, by using the heat monitoring instrument 1 the user can easily and reliably know the state of an increase in the temperature of tissue at a desired location during performance of the thermal therapy.

Fifth Embodiment

A fifth embodiment of the present invention will be described hereunder. Hereunder, only differences with respect to the fourth embodiment are described, and components that are the same as in the fourth embodiment are denoted by the same reference numerals and a description of such components is omitted as appropriate.

Figure 27:
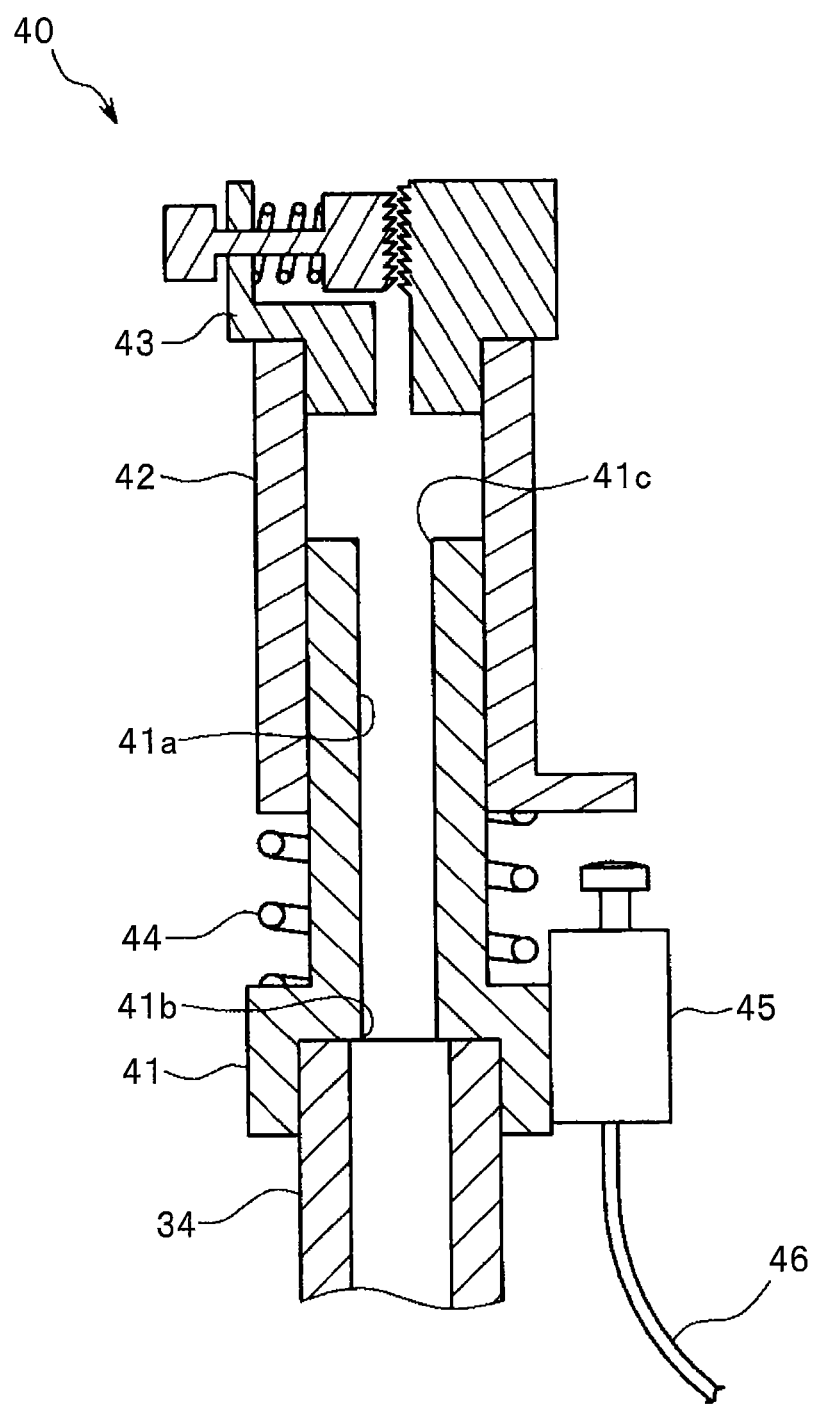
FIG. 27 is a cross-sectional diagram illustrating the configuration of the pulling apparatus of the fifth embodiment.

As shown in FIG. 27, the pulling apparatus 40 of the present embodiment includes a withdrawal detection portion 45 that detects that the insertion portion 2 is withdrawn from the tissue 10 or the cylindrical member 5. The withdrawal detection portion 45 detects the fading of the tensile force T that the pulling apparatus 40 applies to the linear member 4. In a case where the tensile force T fades, the withdrawal detection portion 45 determines that the insertion portion 2 has been withdrawn from the tissue 10 or the cylindrical member 5.

The thermal therapy instrument 20 is connected to a drive apparatus 21 that drives the thermal therapy instrument 20. The thermal therapy instrument 20 and the drive apparatus 21 constitute a thermal therapy apparatus. The withdrawal detection portion 45 is electrically connected to the drive apparatus 21 of the thermal therapy instrument 20 through an electric cable 46.

The drive apparatus 21 actuates the thermal therapy instrument 20 during only a period in which, for example, a footswitch 22 is placed in an "on" state by the user. Further, if withdrawal of the insertion portion 2 from the tissue 10 or the cylindrical member 5 is detected by the withdrawal detection portion 45 during operation of the thermal therapy instrument 20, the drive apparatus 21 stops operation of the thermal therapy instrument 20.

Although the configuration of the withdrawal detection portion 45 is not particularly limited, as shown in FIG. 27, as one example according to the present embodiment, the withdrawal detection portion 45 takes the form of a push switch that is switched on or off in accordance with forward/rearward movement of the slider 42 and the holding portion 43.

Figure 28:
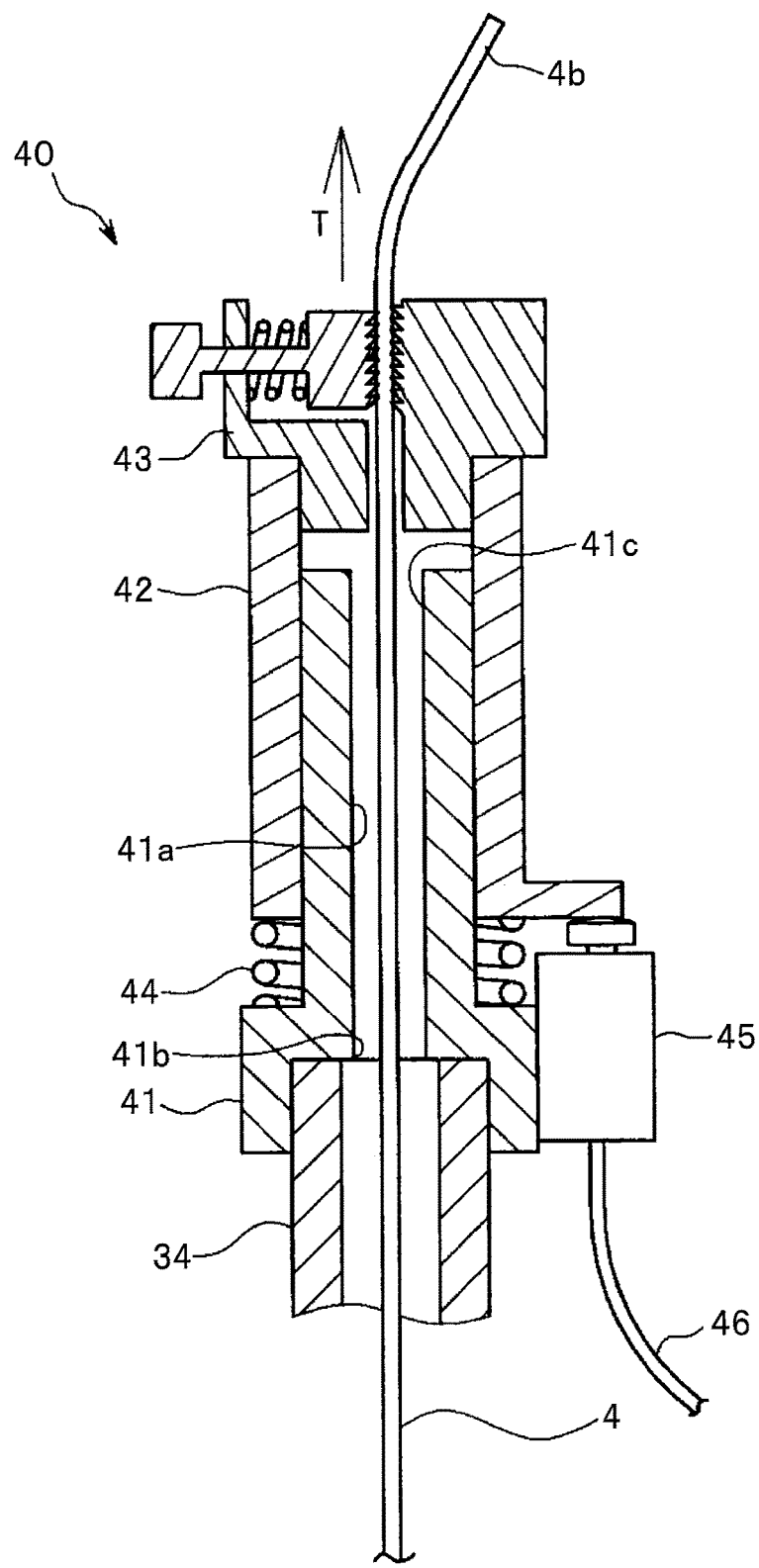
FIG. 28 is a view illustrating a state in which a proximal end portion of the linear member is held by the pulling apparatus of the fifth embodiment.

The withdrawal detection portion 45 that is a push switch is fixed to the base portion 41. As shown in FIG. 28, in a state in which the slider 42 and the holding portion 43 are adjacent to the other end 41c of the through-hole 41a, the withdrawal detection portion 45 comes into contacts with the slider 42 and enters an "on" state. That is, in a state in which the holding portion 43 is brought close to the other end of the other end 41c of the through-hole 41a against the urging force of the urging member 44, the withdrawal detection portion 45 enters an "on" state in a state in which the proximal end portion 4b of the linear member 4 is held by the holding portion 43 and the tensile force T is applied to the linear member 4.

On the other hand, in a state in which the tensile force T is not being applied to the linear member 4, that is, in a state in which the slider 42 and the holding portion 43 are positioned at a location that is separated from the other end 41c of the through-hole 41a by the urging force of the urging member 44, the withdrawal detection portion 45 separates from the slider 42 and enters an "off" state.

When the withdrawal detection portion 45 enters an "off" state during operation of the thermal therapy instrument 20, the drive apparatus 21 stops operation of the thermal therapy instrument 20.

The thermal therapy apparatus of the present embodiment configured as described above automatically stops the thermal therapy instrument 20 in a case where the insertion portion 2 withdraws from the tissue 10 or the cylindrical member 5 during performance of the thermal therapy. Therefore, in a case where the locking portion 3 of the heat monitoring instrument 1 is heated such that the temperature thereof enters the predetermined temperature range that exceeds the predetermined temperature, the thermal therapy instrument 20 can be reliably stopped.

Sixth Embodiment

A sixth embodiment of the present invention will be described hereunder. Hereunder, only differences with respect to the first to fifth embodiments are described, and components that are the same as in the first to fifth embodiments are denoted by the same reference numerals and a description of such components is omitted as appropriate.

In the foregoing embodiments, confirmation of a change in the shape of the insertion portion 2 of the heat monitoring instrument 1 is performed based on a change in a tensile force that is applied to the linear member 4. In contrast, according to the present embodiment, confirmation of a change in the shape of the insertion portion 2 is performed based on the presence/absence of electrical conduction between a pair of electrodes 8*b* provided in the insertion portion 2.

Figure 29:
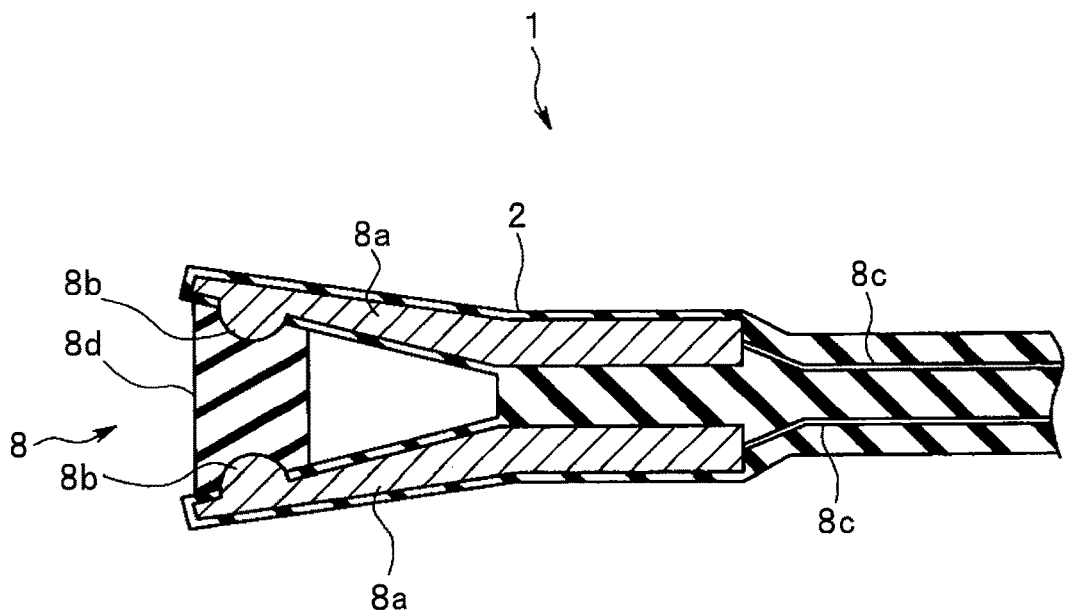
FIG. 29 is a view illustrating the configuration of a heat monitoring instrument according to a sixth embodiment.
Figure 30:
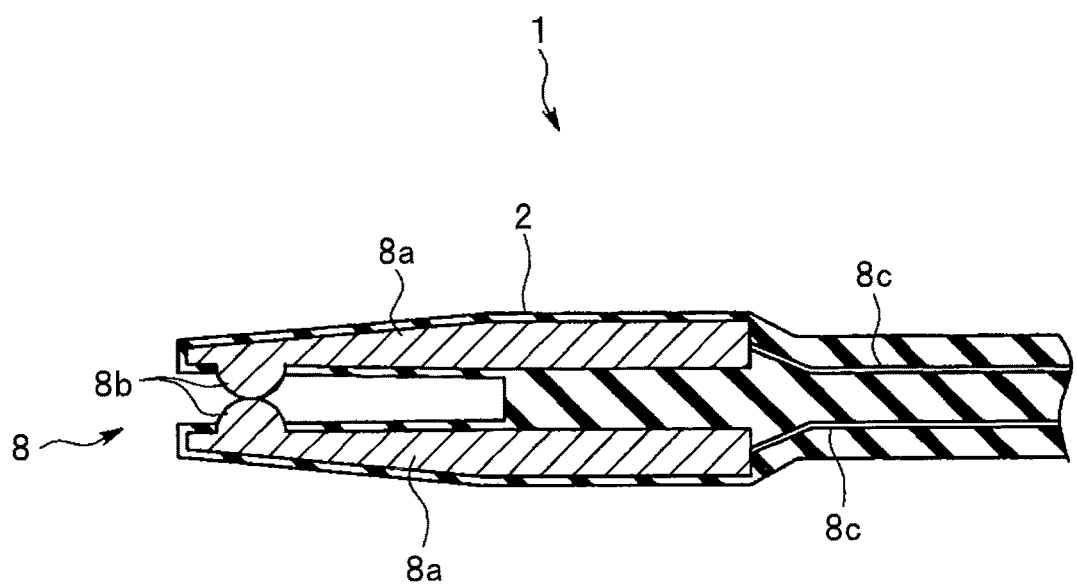
FIG. 30 is a view illustrating a state in which a switch portion changes shape in the heat monitoring instrument of the sixth embodiment.

FIG. 29 illustrates a state before the insertion portion 2 of the heat monitoring instrument 1 changes shape, and FIG. 30 illustrates a state after the insertion portion 2 changes shape.

As shown in FIG. 29, the heat monitoring instrument 1 of the present embodiment includes a switch portion 8 that is arranged at the distal end portion 2*a* of the insertion portion 2. The switch portion 8 includes the pair of electrodes 8*b*, a plate spring 8*a* and an insulating member 8*d*. The pair of electrodes 8*b* are arranged facing each other. The pair of electrodes 8*b* are urged in a direction in which the pair of electrodes 8*b* come in contact with each other by the plate spring 8*a*.

A conductor wire 8*c* extends from each of the pair of electrodes 8*b*. The respective conductor wires 8*c* are electrically connected to an unshown drive apparatus 21 of the thermal therapy instrument 20 through an electric cable. The drive apparatus 21 stops operation of the thermal therapy instrument 20 in a case where electrical conduction is confirmed between the pair of electrodes 8*b* during operation of the thermal therapy instrument 20.

The insulating member 8*d* is pinched between the pair of electrodes 8*b*. The insulating member 8*d* is made of a material that has electrical insulating properties and melts or softens when a predetermined temperature is exceeded. The material constituting the insulating member 8*d* is, for example, beeswax, bone wax or paraffin.

In a case where the temperature of the insertion portion 2 is less than or equal to the predetermined temperature, as shown in FIG. 29, the pair of electrodes 8*b* are separated by the insulating member 8*d* that is interposed therebetween, and electricity is not conducted between the pair of electrodes 8.

If the temperature exceeds the predetermined temperature and the insulating member 8*d* melts or softens, as shown in FIG. 30, the pair of electrodes 8*b* come in contact with each other because of the urging force of the plate spring 8*a*. That is, the switch portion 8 changes shape when the temperature exceeds the predetermined temperature, and establishes electrical conduction between the pair of electrodes 8*b*.

The thermal therapy apparatus of the present embodiment configured as described above automatically stops the thermal therapy instrument 20 in a case where the insertion portion 2 of the heat monitoring instrument 1 changes shape during performance of the thermal therapy. Therefore, in a case where the insertion portion 2 of the heat monitoring instrument 1 is heated such that the temperature thereof enters the predetermined temperature range that exceeds the predetermined temperature, the thermal therapy instrument 20 can be reliably stopped.

Seventh Embodiment

A seventh embodiment of the present invention will be described hereunder. Hereunder, only differences with respect to the sixth embodiment are described, and components that are the same as in the sixth embodiment are denoted by the same reference numerals and a description of such components is omitted as appropriate.

Figure 31:
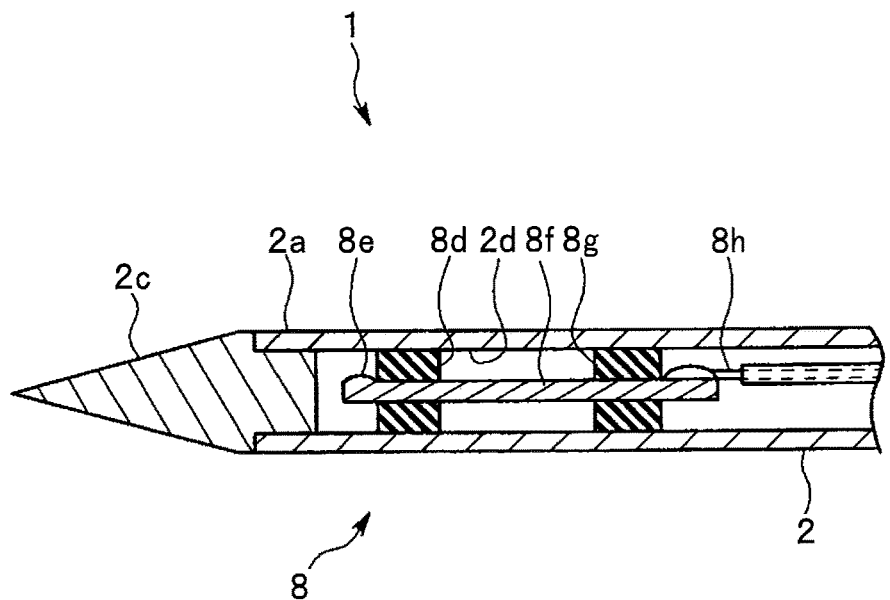
FIG. 31 is a view illustrating the configuration of a heat monitoring instrument according to a seventh embodiment.
Figure 32:
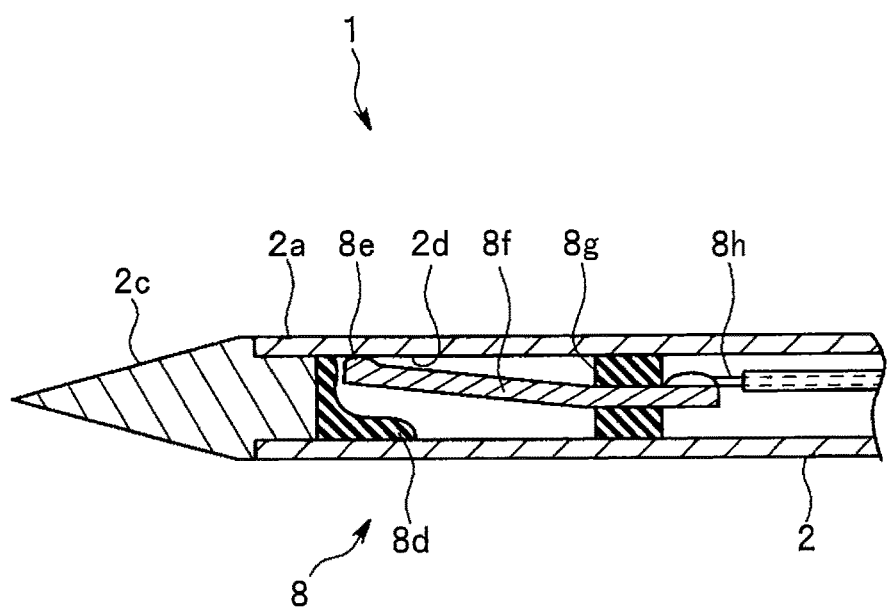
FIG. 32 is a view illustrating a state in which a switch portion changes shape in the heat monitoring instrument of the seventh embodiment.

FIG. 31 illustrates a state before the insertion portion 2 of the heat monitoring instrument 1 changes shape, and FIG. 32 illustrates a state after the insertion portion 2 changes shape.

In the heat monitoring instrument 1 of the present embodiment that is shown in FIG. 31, the distal end portion 2*a* of the insertion portion 2 is formed in a tube shape, and includes the switch portion 8 inside the distal end portion 2*a*. The tubular distal end portion 2*a* is formed of a material having electrical conductivity. Although the material constituting the distal end portion 2*a* is not particularly limited, for example, the distal end portion 2*a* is made of a metal that is biocompatible such as a stainless steel alloy or a Ni—Ti (nickel-titanium) alloy. In this connection, preferably the inner wall face 2*d* of the distal end portion 2*a* is subjected to surface treatment that increases electrical conductivity, such as nickel plating. The internal space of the distal end portion 2*a* that is a tube shape is sealed by a sealing member 2*c*.

The switch portion 8 includes a spring member 8*f*, a holding portion 8*g*, an electrode 8*e* and an insulating member 8*d*. The spring member 8*f* is an elongated rod-shaped or plate-shaped member that is formed of a material having electrical conductivity such as a metal. The proximal end portion of the spring member 8*f* is fixed inside the distal end portion 2*a* by the holding portion 8*g*. The holding portion 8*g* is made of a material having electrical insulating properties.

The electrode 8*e* is formed at the distal end portion of the spring member 8*f*. The spring member 8*f* generates a force that urges the electrode 8*f* in a direction to contact the inner wall face 2*d* of the distal end portion 2*a*.

The insulating member 8*d* is pinched between the electrode 8*e* and the inner wall face 2*d* of the distal end portion 2*a*. The insulating member 8*d* is made of a material that has electrical insulating properties and melts or softens when a predetermined temperature is exceeded. The material constituting the insulating member 8*d* is, for example, beeswax, bone wax or paraffin.

In a case where the temperature of the insertion portion 2 is less than or equal to the predetermined temperature, as shown in FIG. 31, the electrode 8*e* and the inner wall face 2*d* of the distal end portion 2 are separated by the insulating member 8*d* that is interposed therebetween, and electricity is not conducted between the electrode 8*e* and the inner wall face 2*d* of the distal end portion 2.

If the temperature exceeds the predetermined temperature and the insulating member 8*d* melts or softens, as shown in FIG. 32, the electrode 8*e* comes in contact with the inner wall face 2*d* of the distal end portion 2 because of an urging force of the spring member 8*f*. That is, the switch portion 8 changes shape when the temperature exceeds the predetermined temperature, and establishes electrical conduction between the electrode 8*e* and the inner wall face 2*d* of the distal end portion 2.

The electrode 8*e* is electrically connected to the unshown drive apparatus 21 of the thermal therapy instrument 20 through the spring member 8f, a conductor wire 8h that is connected to the spring member 8f, and an electric cable. The inner wall face 2d of the distal end portion 2a is also electrically connected to the unshown drive apparatus 21 of the thermal therapy instrument 20 through an electric cable.

The thermal therapy apparatus of the present embodiment configured as described above automatically stops the thermal therapy instrument 20 in a case where the insertion portion 2 of the heat monitoring instrument 1 changes shape when thermal therapy is performed. Therefore, in a case where the insertion portion 2 of the heat monitoring instrument 1 is heated such that the temperature thereof enters the predetermined temperature range that exceeds the predetermined temperature, the thermal therapy instrument 20 can be reliably stopped.

Further, according to the present embodiment, in comparison to the sixth embodiment, since a situation does not arise in which the melted insulating member 8d comes in contact with the subject, it is not necessary to take into consideration the biocompatibility of the insulating member 8d, and thus the degree of freedom in the selection of the material constituting the insulating member 8d is increased.

Eighth Embodiment

An eighth embodiment of the present invention will be described hereunder. Hereunder, only differences with respect to the sixth embodiment are described, and components that are the same as in the sixth embodiment are denoted by the same reference numerals and a description of such components is omitted as appropriate.

Figure 33:
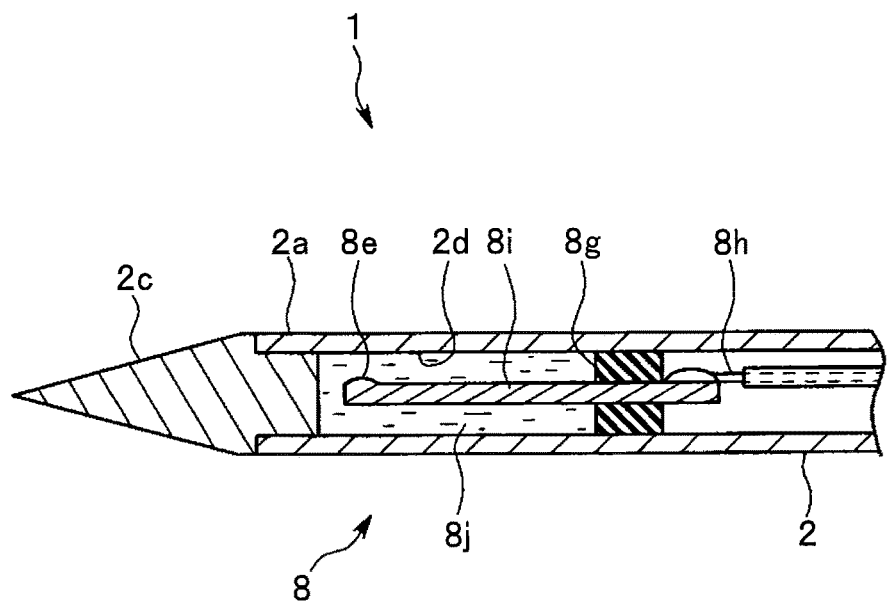
FIG. 33 is a view illustrating the configuration of a heat monitoring instrument according to an eighth embodiment.
Figure 34:
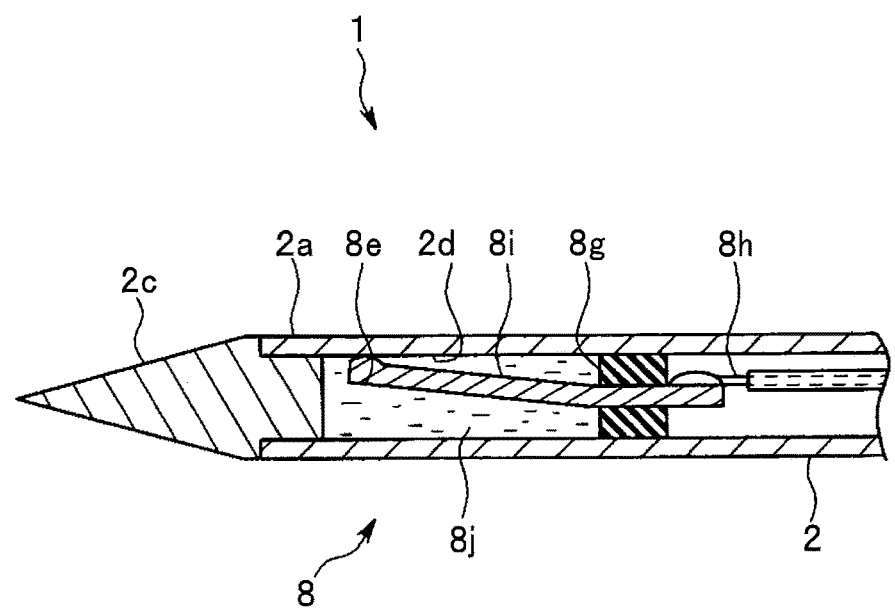
FIG. 34 is a view illustrating a state in which a switch portion changes shape in the heat monitoring instrument of the eighth embodiment.

FIG. 33 illustrates a state before the insertion portion 2 of the heat monitoring instrument 1 changes shape, and FIG. 34 illustrates a state after the insertion portion 2 changes shape.

In the heat monitoring instrument 1 of the present embodiment that is shown in FIG. 33, the distal end portion 2a of the insertion portion 2 is formed in a tube shape, and includes the switch portion 8 inside the distal end portion 2a. The tubular distal end portion 2a is formed of a material having electrical conductivity. Although the material constituting the distal end portion 2a is not particularly limited, for example, the distal end portion 2a is made of a metal that is biocompatible such as a stainless steel alloy or a Ni—Ti (nickel-titanium) alloy. In this connection, preferably the inner wall face 2d of the distal end portion 2a is subjected to surface treatment that increases electrical conductivity, such as nickel plating. The internal space of the distal end portion 2a that is a tube shape is sealed by the sealing member 2c.

The switch portion 8 includes a shape-changing portion 8i, the holding portion 8g, the electrode 8e and a dielectric fluid 8j. The shape-changing portion 8i is constituted by a shape-memory alloy that changes shape when heated to the predetermined temperature range that exceeds the predetermined temperature. A proximal end portion of the shape-changing portion 8i is fixed to the inside of the distal end portion 2a by the holding portion 8g. The holding portion 8g is made of a material having electrical insulating properties.

The electrode 8e is formed at a distal end portion of the shape-changing portion 8i. Further, the internal space of the distal end portion 2a is filled with the dielectric fluid 8j that is a liquid that has electrical insulating properties.

When the shape-changing portion 8i that is made of a shape-memory alloy is less than or equal to the predetermined temperature, as shown in FIG. 33, the shape-changing portion 8i becomes an approximately rectilinear shape that extends in the longitudinal direction of the distal end portion 2 so that the electrode 8e and the inner wall face 2d of the distal end portion 2 are separated. That is, in this case, electricity is not conducted between the electrode 8e and the inner wall face 2d of the distal end portion 2.

On the other hand, when the shape-changing portion 8i exceeds the predetermined temperature, as shown in FIG. 34, the shape-changing portion 8i becomes a bent shape so that the electrode 8e and the inner wall face 2d of the distal end portion 2 come in contact. That is, in this case, electricity is conducted between the electrode 8e and the inner wall face 2d of the distal end portion 2.

As described above, the switch portion 8 changes shape when the temperature exceeds the predetermined temperature, and establishes electrical conduction between the electrode 8e and the inner wall face 2d of the distal end portion 2. The dielectric fluid 8j that is filled inside the distal end portion 2 serves a role of transmitting the temperature of the distal end portion 2 to the shape-changing portion 8i of the switch portion 8. Accordingly, if the temperature of the distal end portion 2 is less than or equal to the predetermined temperature, the electrode 8e of the switch portion 8 and the inner wall face 2d of the distal end portion 2 enter an electrically insulated state, and if the temperature of the distal end portion 2 exceeds the predetermined temperature, the electrode 8e of the switch portion 8 and the inner wall face 2d of the distal end portion 2 enter an electrically conducting state.

The electrode 8e is electrically connected to the unshown drive apparatus 21 of the thermal therapy instrument 20 through the shape-changing portion 8i, a conductor wire 8h that is connected to the shape-changing portion 8i, and an electric cable. The inner wall face 2d of the distal end portion 2a is also electrically connected to the unshown drive apparatus 21 of the thermal therapy instrument 20 through an electric cable.

The thermal therapy apparatus of the present embodiment configured as described above automatically stops the thermal therapy instrument 20 in a case where the insertion portion 2 of the heat monitoring instrument 1 changes shape when thermal therapy is performed. Therefore, in a case where the insertion portion 2 of the heat monitoring instrument 1 is heated such that the temperature thereof enters the predetermined temperature range that exceeds the predetermined temperature, the thermal therapy instrument 20 can be reliably stopped.

The present invention is not limited to the above described embodiments, and may be suitably changed without departing from the spirit or concept of the invention readable from the appended claims and the entire specification, and a heat monitoring instrument and a thermal therapy apparatus with such changes are also included in the technical scope of the present invention.

[Supplementary Note 1]

A heat monitoring instrument including: an insertion portion to be inserted into tissue of a subject; and a switch portion that is provided in the insertion portion, and changes shape when heated from a state of a predetermined temperature or less to a predetermined temperature range that exceeds the predetermined temperature so that presence/absence of electrical conduction is switched.

[Supplementary Note 2]

The heat monitoring instrument according to supplementary note 1, wherein the insertion portion is composed of a tubular member in which a distal end portion is sealed, and the switch portion is arranged inside the distal end portion of the insertion portion.

[Supplementary Note 3]

A thermal therapy apparatus that includes a heat monitoring instrument according to supplementary note 1 or 2, a thermal therapy instrument that heats the tissue, and a drive apparatus that actuates the thermal therapy instrument; wherein in a case where switching of presence/absence of electrical conduction of the switch portion of the heat monitoring instrument is detected, the drive apparatus stops operation of the thermal therapy instrument.

What is claimed is:

1. A heat monitoring instrument, comprising:
   an insertion portion for inserting into tissue of a subject;
   a locking portion provided on a distal end portion of the insertion portion, the locking portion being configured to engage with the tissue by being bent in a hook-like shape when the locking portion is at a predetermined temperature or less, and to eliminate being bent and release the engagement with the tissue when the locking portion is heated from the predetermined temperature or less to a predetermined temperature range that exceeds the predetermined temperature;
   a linear member, a distal end portion of which is coupled to the insertion portion;
   a holding portion configured to hold a proximal end portion of the linear member and to move in a distal end direction and a proximal end direction of the linear member;
   an urging member configured to urge the holding portion in the proximal end direction to apply a tensile force to the linear member; and
   a detection portion configured to detect movement of the linear member and the holding portion in the proximal end direction when the engagement of the locking portion with the tissue is released.

2. The heat monitoring instrument according to claim 1, further comprising a cylindrical member, a distal end side of which has a cylindrical shape configured to be pierced into the tissue, and an inside of which the insertion portion can be inserted into.

3. A thermal therapy apparatus, comprising:
   the heat monitoring instrument according to claim 1,
   a thermal therapy instrument that heats the tissue, and
   a drive apparatus that actuates the thermal therapy instrument;
   wherein the drive apparatus stops operation of the thermal therapy instrument in a case where the detection portion detects the movement of the holding portion in the proximal end direction during operation of the thermal therapy instrument.

4. The heat monitoring instrument according to claim 1, further comprising a base fixed to a proximal end-side opening of a treatment instrument channel of an ultrasound endoscope.

5. The heat monitoring instrument according to claim 4, further comprising a slider to which the holding portion is fixed, the slider being configured to move relatively with respect to the base by being urged by the urging member.

6. The heat monitoring instrument according to claim 5, wherein the slider includes the holding portion configured to hold a proximal end portion of the linear member.

\* \* \* \* \*